(12) United States Patent
Jones

(10) Patent No.: US 7,799,029 B2
(45) Date of Patent: Sep. 21, 2010

(54) RADIAL IMPACTION BONE TAMP AND ASSOCIATED METHOD

(75) Inventor: Michael C. Jones, North Webster, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 688 days.

(21) Appl. No.: 10/671,820

(22) Filed: Sep. 26, 2003

(65) Prior Publication Data
US 2005/0070898 A1 Mar. 31, 2005

(51) Int. Cl.
*A61B 17/56* (2006.01)

(52) U.S. Cl. .................. 606/53; 606/68; 623/22.12

(58) Field of Classification Search .............. 606/53, 606/60, 62–63, 86, 88, 67–68; 425/469; 411/80.1, 80.2, 80.5; 623/23.11–23.38, 20.35–20.36, 623/22.12
See application file for complete search history.

(56) References Cited

U.S. PATENT DOCUMENTS

| | | | | |
|---|---|---|---|---|
| 832,201 | A | * | 10/1906 | Kistler ............... 604/108 |
| 2,601,803 | A | * | 7/1952 | Newman ............ 411/80.1 |
| 2,620,537 | A | * | 12/1952 | Gobin-Daude ......... 411/21 |
| 3,779,239 | A | * | 12/1973 | Fischer et al. ......... 606/63 |
| 3,921,496 | A | * | 11/1975 | Helderman ............ 411/17 |
| 4,204,531 | A | * | 5/1980 | Aginsky .............. 606/63 |
| 4,237,875 | A | * | 12/1980 | Termanini ............ 606/63 |
| 4,275,717 | A | * | 6/1981 | Bolesky ............. 606/63 |
| 4,462,394 | A | * | 7/1984 | Jacobs ............... 606/94 |
| 4,519,100 | A | * | 5/1985 | Wills et al. .......... 606/63 |
| 5,047,035 | A | | 9/1991 | Mikhail et al. |
| 5,057,103 | A | * | 10/1991 | Davis ................ 606/63 |
| 5,089,004 | A | | 2/1992 | Averill et al. |
| 5,108,405 | A | | 4/1992 | Mikhail et al. |
| 5,129,283 | A | | 7/1992 | Koehler |
| 5,147,408 | A | | 9/1992 | Noble et al. |
| 5,180,388 | A | | 1/1993 | DiCarlo |
| 5,197,967 | A | | 3/1993 | Wilson |
| 5,222,955 | A | | 6/1993 | Mikhail |
| 5,222,985 | A | | 6/1993 | Homsy |
| 5,234,433 | A | | 8/1993 | Bert et al. |
| 5,312,412 | A | | 5/1994 | Whipple |
| 5,324,293 | A | | 6/1994 | Rehmann |
| 5,385,566 | A | | 1/1995 | Ullmark |
| 5,601,564 | A | | 2/1997 | Gustilo et al. |
| 5,658,293 | A | | 8/1997 | Vanlaningham |
| 5,718,707 | A | | 2/1998 | Mikhail |
| 5,755,720 | A | | 5/1998 | Mikhail |

(Continued)

FOREIGN PATENT DOCUMENTS

DE         3630069 C1  *  9/1986

(Continued)

OTHER PUBLICATIONS

European Search Report dated Sep. 22, 2005, for corresponding EP application 04255788.4.

*Primary Examiner*—Thomas C Barrett
*Assistant Examiner*—James L. Swiger

(57) ABSTRACT

An instrument for compacting bone material is provided. The instrument includes a first component defining a longitudinal axis of the first component and a second component. The second component is moveably associated with the first component. The second component is moveable at least partially in a radial direction outwardly from the longitudinal axis of the first component.

12 Claims, 18 Drawing Sheets

U.S. PATENT DOCUMENTS

| | | |
|---|---|---|
| 5,766,178 A | 6/1998 | Michielli et al. |
| 5,788,704 A | 8/1998 | Timperley |
| 5,897,560 A | 4/1999 | Johnson |
| 5,928,240 A | 7/1999 | Johnson |
| 5,935,169 A | 8/1999 | Chan |
| 6,013,080 A | 1/2000 | Khalili |
| 6,015,408 A | 1/2000 | Pichon et al. |
| 6,139,583 A | 10/2000 | Johnson |
| 6,142,998 A | 11/2000 | Smith et al. |
| 6,143,030 A | 11/2000 | Schroder |
| 6,149,669 A * | 11/2000 | Li ............... 606/232 |
| 6,228,092 B1 | 5/2001 | Mikhail |
| 6,248,110 B1 | 6/2001 | Reiley et al. |
| 6,270,502 B1 | 8/2001 | Stulberg |
| 6,309,220 B1 | 10/2001 | Gittleman |
| 6,354,779 B1 * | 3/2002 | West et al. ........... 411/80.1 |
| 2002/0058949 A1 | 5/2002 | Iaia |
| 2002/0065518 A1 * | 5/2002 | Naybour et al. ........ 606/86 |
| 2004/0087994 A1 * | 5/2004 | Suddaby ............... 606/190 |

FOREIGN PATENT DOCUMENTS

| | | |
|---|---|---|
| DE | 3630069 C1 * | 1/1988 |
| DE | 19949385 C2 | 5/2002 |
| EP | 0 006 314 A1 | 1/1980 |
| EP | 0 178 174 A2 | 4/1986 |
| EP | 0 121 142 B1 | 7/1987 |
| EP | 0 139 520 B1 | 5/1988 |
| EP | 0 586 824 A1 | 3/1994 |
| EP | 0 595 956 B1 | 9/1998 |
| EP | 0 700 272 B1 | 1/1999 |
| EP | 0 913 136 A3 | 7/1999 |
| EP | 0992225 A2 * | 4/2000 |
| EP | 0992225 A2 | 4/2000 |
| EP | 0992225 A3 | 4/2000 |
| EP | 0 705 579 B1 | 7/2002 |
| EP | 1208821 B1 | 7/2004 |
| WO | WO 92/02183 A1 | 2/1992 |
| WO | WO 96/25113 A1 | 8/1996 |
| WO | WO 98/29045 A1 | 7/1998 |
| WO | WO 01/17444 A1 | 3/2001 |

* cited by examiner

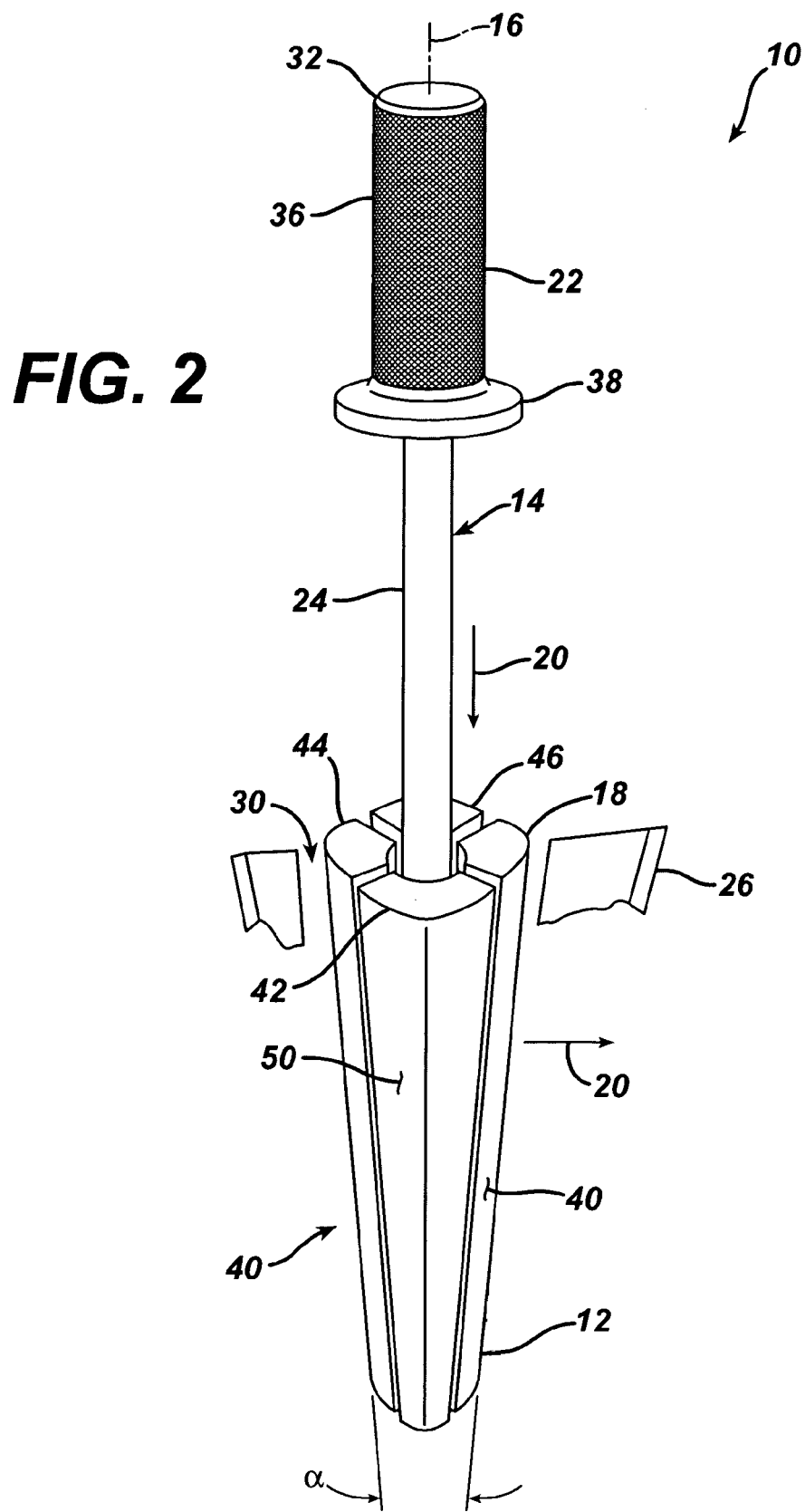

RADIAL IMPACTION BONE TAMP AND ASSOCIATED METHOD

TECHNICAL FIELD OF THE INVENTION

The present invention relates generally to the field of orthopaedics, and more particularly, to an instrument for use in arthroplasty.

BACKGROUND OF THE INVENTION

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the motion of sliding, gliding, hinge or ball and socket movements may be had by a joint. For example, the ankle permits a hinge movement, the knee allows for a combination of gliding and hinge movements and the shoulder and hip permit movement through a ball and socket arrangement.

The joints in the body are stressed or can be damaged in a variety of ways. For example, the gradual wear and tear is imposed on the joints through the continuous use of a joint over the years. The joints that permit motion have cartilage positioned between the bones providing lubrication to the motion and also absorbing some of the forces direct to the joint. Over time, the normal use of a joint may wear down the cartilage and bring the moving bones in a direct contact with each other. In contrast, in normal use, a trauma to a joint, such as the delivery of a large force, from an accident, for example, an automobile accident, may cause considerable damage to the bones, the cartilage or to other connective tissue such as tendons or ligaments.

Arthropathy, a term referring to a disease of the joint, is another way in which a joint may become damaged. Perhaps the best known joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthritis is osteonecrosis, which is caused by the death of a part of the bone due to loss of blood supply. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted with arthropathy. The hip joint is a ball and socket joint that joins the femur or thigh bone with the pelvis. The pelvis has a semispherical socket called the acetabulum for receiving a ball socket head in the femur. Both the head of the femur and the acetabulum are coated with cartilage for allowing the femur to move easily within the pelvis. Other joints commonly afflicted with arthropathy include the spine, knee, shoulder, carpals, metacarpals, and phalanges of the hand. Arthroplasty as opposed to arthropathy commonly refers to the making of a artificial joint. In severe cases of arthritis or other forms of arthropathy, such as when pain is overwhelming or when a joint has a limited range of mobility, a partial or total replacement of the joint within an artificial joint may be justified. The procedure for replacing the joint varies, of course, with the particular joint in question, but in general involves replacing a terminal portion of an afflicted bone with a prosthetic implant and inserting a member to serve as a substitute for the cartilage.

The prosthetic implant is formed of a rigid material that becomes bonded with the bone and provides strength and rigidity to the joint and the cartilage substitute members chosen to provide lubrication to the joint and to absorb some of the compressive forces. Suitable material for the implant include metals, and composite materials such as titanium, cobalt chromium, stainless steel, ceramic and suitable materials for cartilage substitutes include polyethylene. A cement may also be used to secure the prosthetic implant to the host bone.

A total hip replacement, for example, involves removing the ball shaped head of the femur and inserting a stem implant into the center of the bone which is referred to as the medullary canal or marrow of the bone. The stem implant may be cemented into the medullary canal or may have a porous coated surface for allowing the bone to heal directly to the implant. The stem implant has a neck and a ball shaped head which are intended to perform the same functions as a healthy femur's neck and a ball shaped head. The polyethylene cup is inserted into the acetabulum and has a socket for receiving the head on the stem implant.

Unfortunately, some patients who have undergone partial or total joint replacements require revision surgery. Revision surgery may be required soon after the primary surgery or may not be needed for years. Revision surgery may be required for one of a number of reasons. For one, fixation of the joint may be compromised. A trauma of to the joint may result in the loosening or the loosening of the joint may have been caused by other factors, such as an insufficient bond between the implant and the host bone. The loosening of an implant can be quite painful and also can pose danger to the patient. For example, movement of the loose implant within the bone may fracture the bone itself.

Revision surgery may be necessary for other reasons. For example, particle debris from the cartilage substitute member or even from any of the other implants may cause osteolysis in the patient. In general osteolysis is the body's natural immune response to foreign objects which result in inflammation and pain in the joint. Another reason why revision surgery may be necessary, is due to death of part of the bone. A bone requires stress in order to remain strong and any bone that is not stressed will become weak and fragile. This result is often known as Wolf's Law. The insertion of an implant may stress shield portions of the bone whereby these portions no longer receive the stress that it requires in order to remain strong. Another reason to perform revision surgery is to take advantage of advancements in prosthetic design. Thus, for many reasons, revision surgery may be necessary or desirable for a patient.

Revision surgery is more complicated than the primary partial or total joint replacements since it requires removal of the previously inserted stem implant and introduction of another stem implant. When the stem implant is removed, a portion of the surrounding tissue is removed along with the implant. If cement was used to secure the original implant, then additional tissue is normally removed to insure that all the cement has been removed from within the medullary canal. When cement is not used, often a porous surface is formed on the implant to promote bony ingrowth. This area around the bony ingrowth may need to be removed and may require tools to separate the prosthesis from the bone. During a revision surgery, this void left by the removal of the surrounding tissue must be filled in order to allow the stem implant to bond with the host bone.

Surgical techniques have been developed for the revision of the hip system. In these prior arts systems, bone may be harvested from another portion of the patient to form an autograft which may be tamped in positioned in the bone cavity, for example the femur. Alternatively, substitute bone material may be used. Such bone material may be an allograft or human tissue available from a tissue bank or may be artificial tissue obtained from Pro Osteon™ available from Interpore, 181 Technology Drive, Irvine, Calif. A small portion of the autograft, the allograft, or the artificial bone material is bone is inserted into the femur and packed and the process is repeated until a portion of the femur has been filled.

A tamping process may be performed which packs material into the medullary canal until the bone cavity is the proper size for the stem implant. This process may include the use of progressively large tamps until a tamp representing the size and shape of the implant's stem is used.

After the packing of the canal is complete, blood pooled at the distal end of the stem may be extracted with suction applied in the tamp. The tamp is then removed just immediately prior to the insertion of the cement into the canal. A cement gun with a nozzle cut off to the length of the stem is use to inject cement into the narrow distal stem area. A second, larger nozzle may then be used to complete the filling of the proximal femur and to pressurize the cement. The stem is inserted and the pressure maintained until the cement has polymerized.

This method is wrought with several problems. One of these problems is that in order to tamp the morselized bone into the cavity, the distal portion of the cavity must first be filled and a large quantity of graft material must be used. It may be traumatic for the patient as additional morselized bone must be harvested from the patient. Conversely, when bone substitute material issues, a larger and more expensive amount of material must be used. Further the packing of the entire canal may cause additional blood loss and blood flow as the blood is absorbed and moved toward the open portion of the cavity as the material continues to be packed by the tamps.

Further, the use of the tamps create a limit on the shape of the cavity created by the tamp as well as limiting the precision of the fit of the tamp to the prosthesis stem.

The present invention is aimed at alleviating at least some of the aforementioned problems.

SUMMARY OF THE INVENTION

The present invention provides for an instrument and related surgical technique that prepares the medullary canal by radial impaction of the morselized bone graft or allograft. The instrument provides for compacting bone graft material without compacting the bone distally at the same time. Thus, the present invention provides for a cavity receiving the distal stem without totally filling the canal distally to achieve the radial fill of the canal. The present invention provides for such a radial impaction of the bone graft by providing a two piece instrument with a first piece for insertion partially into the bone cavity and a second portion for moving radially outwardly toward the inner wall of the bone cavity to radially impact the morselized bone graft.

According to one embodiment of the present invention, an instrument for compacting bone material is provided. The instrument includes a first component defining a longitudinal axis of the first component and a second component. The second component is moveably associated with the first component. The second component is moveable at least partially in a radial direction outwardly from the longitudinal axis of the first component.

According to another embodiment of the present invention there is provided an instrument for compacting bone material in a medullary canal of a long bone. The instrument includes a first component defining a longitudinal axis of the first component. The first component has an outer periphery having a portion of the outer periphery which is tapered along the longitudinal axis. The portion of the outer periphery of the first component defines a restraining portion of the outer periphery. The first component also has a second component moveably associated with the first component. The second component defines a cooperating portion for cooperating with the restraining portion of the first component to provide restrained motion of the second component with respect to the first component.

According to a further embodiment of the present invention, there is provided a method for preparing a cavity in a long bone. The method includes the steps of cutting an incision in the patient, preparing a cavity in a long bone, providing an instrument for compacting bone material having a first component defining a longitudinal axis thereof and a second component moveable at least partially in a radial direction outwardly from the longitudinal axis of the first component, placing the instrument in the cavity, and compacting bone material in the cavity.

The technical advantages of the present invention include the ability to provide radial impacting of bone graft material without filling the cavity distally and, thereby, with the use of a minimal amount of bone graft material. For example, according to one aspect of the present invention, an instrument is provided with a first component which is moveable radially with respect to a second component to urge the bone material against the cortical wall of the long bone. Thus, the present invention provides for radial impacting of bone graft material without filling the cavity distally and with a minimal amount of bone graft material required.

The technical advantage of the present invention further include the ability to provide for a greater radial impacting force. This greater impaction force may provide improved compaction of the bone graft material. For example, according an aspect of the present invention, an instrument is provided with a first component moveable radially with respect to a second component with the component which is moveable radially with respect to the longitudinal movement of the second component importing radial impaction force on the bone graft material. Thus, the present invention provides for greater radial impaction force and improved impaction of the bone graft material.

Yet another technical advantage of the present invention includes the ability to provide a cavity for receiving an implant formed of bone graft material which provides a shape that matches the implant. For example, according an aspect of the present invention, the outer periphery of a first component which is moveable radially with respect to a second component, may have a outer contour with a shape to conform with the prosthesis such that, as the instrument is used, the outer periphery of the instrument forms a cavity formed of the bone graft material which matches the shape of the implant. Thus, the present invention provides for a shape of a cavity that matches the shape of the implant. Such matching of the shape of the cavity of bone graft material to the implant provides for improved stability of the implant in the long bone.

Yet another technical advantage of the present invention is the ability of the instrument of the present invention to replace a set of tamps with one instrument or tamp of the present invention. The ability to replace a set of tamps with a solitary instrument of the present invention will result in reduced inventory and reduced inventory cost and manufacturing cost for manufacturing a large quantity of sets of tamps.

Prior art systems utilize a series of progressively larger tamps to form the cavity within the bone graft material. By providing the tamp of the present invention, a solitary tamp which expands readily outward will replace this series of tamps. For example, according to one aspect of the present invention, an instrument is provided with a first component moveable radially with respect to a second component to urge the bone material against the cortical wall of the bone. The radial motion of the first tamp provides for a tamp which can replace the set of progressively larger diameter tamps that would otherwise be required. Thus, the present invention provides for a solitary instrument to replace a set of multiple tamps.

Another advantage of the present invention includes the ability to reduce the time of performing an arthroplasty. For example, according to one aspect of the present invention, an instrument is provided with a first component moveable radially with respect to a second component to urge the bone material against the cortical wall of the bone. The instrument of the present invention is struck on the end of the instrument and the final form of the cavity for the implant is formed in one insertion of one instrument and one tamping of the instrument. In prior arts systems a multitude of progressively larger tamps must be separately inserted and removed from the cavity and separately struck to compact the bone graft material. Thus, the present invention provides for a reduction in the time to perform an arthroplasty.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 2 is a perspective view of the instrument of FIG. 1;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
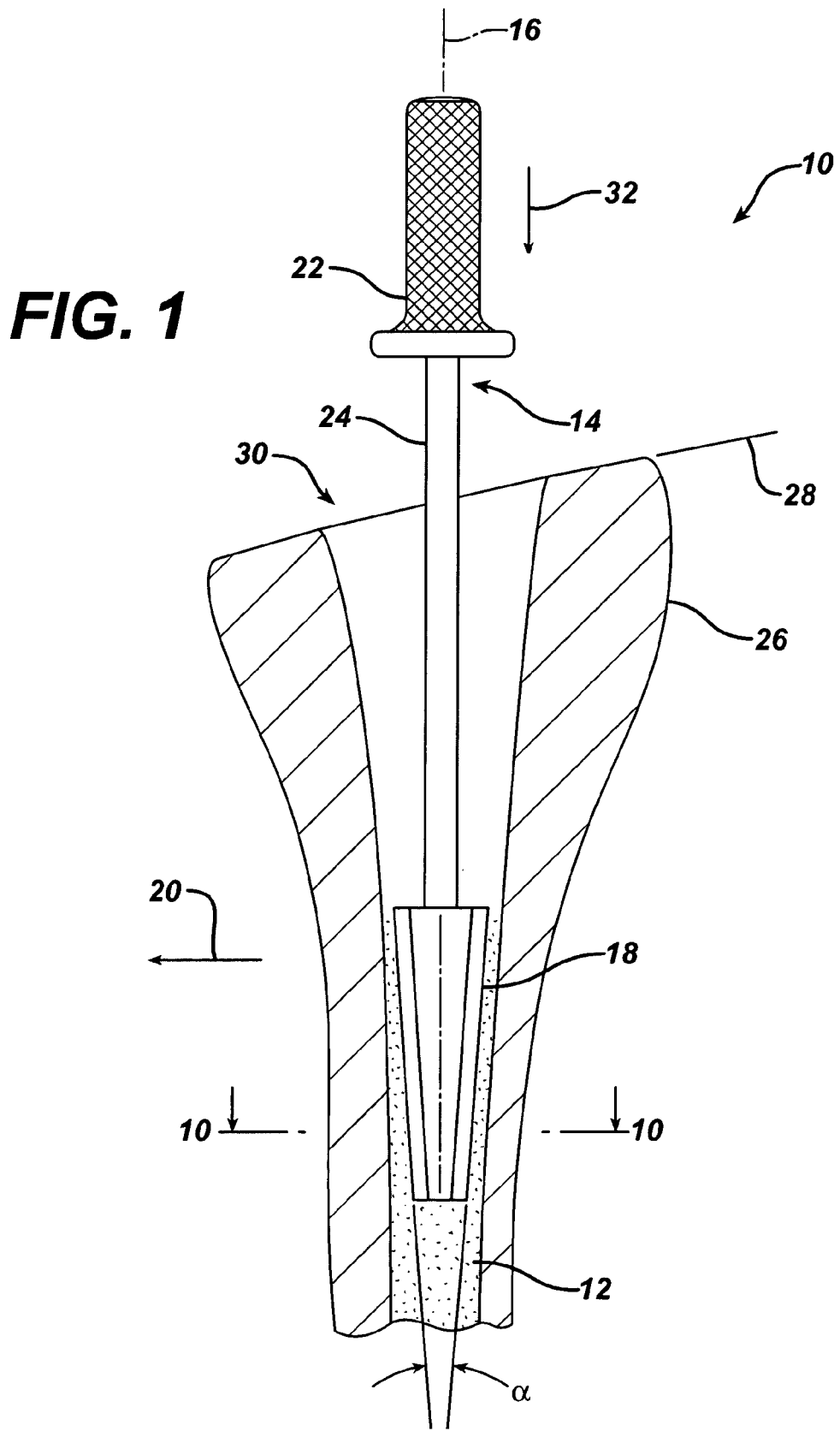
FIG. 1 is a plan view partially in cross section of an instrument in accordance with the present invention in position in a bone.

According to the present invention and referring now to FIG. 1, an instrument 10 for compacting bone material 12 is shown. The instrument 10 includes a first component 14 defining a longitudinal axis 16 of the first component 14. The instrument 10 also includes a second component 18 which is moveably associated with the first component 14. The second component 18 is moveable at least partially in a radial direction 20 outwardly from the longitudinal axis 16 of the first component 14.

The first component 14 may, for example, include a body 22 and a stem 24 extending from the body 22. The second component 18 may, for example, be slidably mounted to the stem 24.

The instrument 10 may be configured, for example, such that the first component 14 or the second component 18 is tapered along the longitudinal axis 16. For example, both the first component 14 and the second component 18 may be tapered along the longitudinal axis.

Shown in FIG. 1, the instrument 10 may be used for example in conjunction with a long bone 26. For example, the long bone 26 may be a femur, a tibia, a fibula, a humerus, an ulna, a radius, or any long bone in the skeletal system of a body.

The instrument 10 is utilized to prepare a cavity for an implant. The instrument 10 is used to impact or tamp bone material 12. To utilize the instrument 10, the long bone 26 is resected along resection line 28. Drills, reamers, and broaches and other instruments may be utilized to prepare medullary canal 30. While the instrument 10 may be utilized to assist in preparing the medullary canal 30 for a primary implant, it should be appreciated that the instrument 10 is particularly well suited for use with revision surgery.

When utilizing the instrument 10 in conjunction with revision surgery, an existing prosthetic component (not shown) placed in the canal 30 of the long bone is removed. During the removal process of the original or primary implant stem, additional bone and other tissue is inadvertently removed with the failed prosthetic stem. If the original or primary prosthetic stem was implanted without cement, bone material may have grown or adhered to the surface of the prosthesis and additional bone maybe required to be remove around the stem to loosen the stem for its removal. Similarly, if the original or primary prosthesis was used with cement, the prosthesis as well as the cement adjoining the prosthesis will need to be removed to permit a revision surgery. In either case, with a revision surgery, whether the original stem was cemented or uncemented, additional bone and soft tissue are removed during the extraction of the failed prosthesis.

The soft tissue and bone removed must be replaced to permit the installation of a revision prosthesis. Bone material 12 in the form of, for example, an autograft of the patient from another location of the patient, an allograft (human tissue from a tissue bank), or synthetic bone material such as Pro Osteon™ from Interpore, 181 Technology Drive, Irvine, Calif., may be needed to prepare the medullary canal 30. As shown in FIG. 1 the bone material 12 must first be positioned in the medullary canal 30 and the instrument 10 inserted in the direction of arrow 32 into the medullary canal 30.

Referring now to FIG. 2, the instrument 10 is shown in greater detail. The first component 14 may have any suitable shape capable of cooperating with the second component 18 and capable of clearance within the medullary canal 30. It should be appreciated that the first component 14 may have an uniform cross section along the longitudinal axis 16 and may have a simple cross section, for example, a circular cross section or a rectangular cross section. The portion of the first component 14 that passes into the medullary canal 30 preferably has a profile small enough for clearance with the canal 30.

The proximal end 32 of the first component 14 may include a feature for assisting in moving the first component 14 in longitudinal direction 34. For example, and as shown in FIG. 2, the first component 14 may include the body 22 which extends from the stem 24. The body 22 may be in the form of a handle and may be elongated along the longitudinal axis 16 and it may have, for example, a circular cross section. The body 22 may include knurls 36 on the periphery of the body 22 for assisting in gripping the instrument 10. A flange 38 may be positioned between the body 22 and the stem 24 for assisting and providing additional force on the instrument 10 in the direction of longitudinal direction 34.

The second component 18 defines an outer periphery 40 thereof. In order that the instrument 10 provides the most compatible surface for the prosthesis that is implanted in the canal 30, the outer periphery 40 of the second component 18 preferably has a shape that replicates the outer periphery of the prosthesis. Depending on the shape of the stem of the prosthesis, the outer periphery 40 may be cylindrical, have any polygon or other shape and may or may not be tapered. The outer periphery 40 may be defined by an included angle α thereof.

While the present invention may be practiced with an instrument 10 having a solitary second component 18, in order that outer periphery 40 of second component 18 replicate the stem of a prosthesis, and in order that the outer periphery 40 of the second component 18 be moveable in the radial direction 20, the second component 18 must either be resilient or additional components must cooperate with the first component 14 and likewise be moveable in the radial direction 20. Conversely, the second component 18 may in the form of a collet and include a series of slits to provide a resilient nature to the second component 18.

The instrument 10 may further include a third component 42 moveably associated with the first component 14. The third component 42 is moveable at least partially in the radial direction 20 outwardly from the longitudinal axis 16 of the first component 14. In addition to the third component 42, the instrument 10 may further include a fourth component 44 moveably associated with the first component 14. The fourth component may be moveable at least partially in a radial direction 20 outwardly form the longitudinal axis 16 of the first component 14.

In addition to the second component 18, the third component 42 and the fourth component 44, the instrument 10 of the present invention may further include a fifth component 46.

The fifth component 46 may be moveable at least partially in the radial direction 20 outwardly from the longitudinal axis 16 of the first component 14. Each of the second component 18, third component 42, fourth component 44, and fifth component 46 act to concert to form outer periphery 50 of the tamping portion 48 of the instrument 10.

Figure 3:
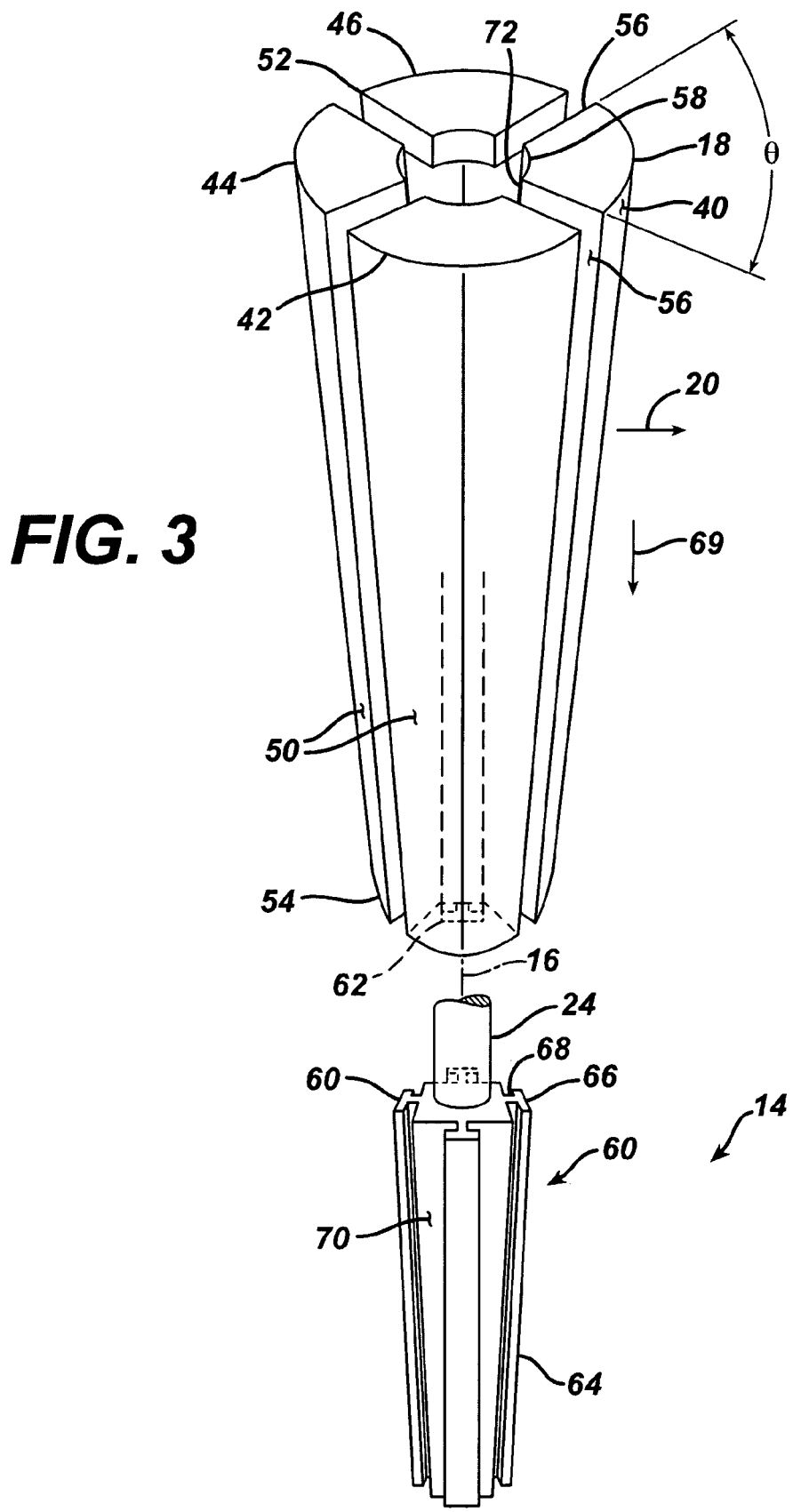
FIG. 3 is a partial exploded perspective view of the instrument of FIG. 1.

Referring now to FIG. 3, the tamping portion 48 of the instrument 10 is shown in greater detail. While the tapping portion 48 may be made of a single component, to provide for radial displacement in the radial direction 20, the tamping portion 48 as shown in FIG. 3 includes a plurality of components. Each of these plurality of components may move with respect to each other so that the tapping portion is moveable in the radial direction 20. Such multi piece construction provides for the opportunity to use strong and durable components.

If the tamping portion 48 is made of plurality of components, it should be appreciated that the tamping portion 48 may include two, three, four, or more components. For example, and as shown in FIG. 3, the tapping portion 48 includes the four components. The components are second component 18, third component 42, fourth component 44, and fifth component 46. It should be appreciated that each of the components may be identical to each other or each component may be somewhat different in size and shape from the other components.

As shown in FIG. 3, for simplicity, the second component 18, third component 42, and fourth component 44, as well as, the fifth component 46 are each identical to each other. The second component 18 will be described in greater detail. The second component 18 includes the second component outer periphery 40. The periphery 40 preferably corresponds to a portion of periphery 8 of the distal portion 6 of stem 4 (see FIG. 1A). Thus, the periphery 40 is preferably arcuate. The periphery 40 as shown in FIG. 3 may extend generally linearly and may be tapered inwardly along the longitudinal axis 16 from proximal end 52 to distal end 54 of the tamping portion 48. The second component 18 further includes a pair of spaced apart radial side walls 56. The side walls 56 extend gradually outward from the longitudinal axis 16 of the instrument 10. The side walls 56 form an included angle θ there between. When the tamping portion 48 includes four components, the angle θ is approximately 90 degrees. The tamping portion 48, as shown in FIG. 3, may include a proximal internal lip 58 extending inwardly from proximal end 52 of the tapping portion 48. The lip 58 may be utilized to limit the motion of the second component 18 in the distal direction 60 along the longitudinal axis 16.

While the instrument of the present invention may be practiced with a second component moveably associated with the first component, the second component may be interconnected or restrained within the first component so that the instrument may be easily inserted and removed from the cavity 30 of the long bone 26. For example, and as shown in FIG. 3, the instrument 10 may include a restraining portion 60 that cooperates with a cooperating portion 62 of the second component 18. The restraining portion 60 and the cooperating portion 62 provide for restraining the motion of the second component 18 with respect to the first component 14. To accommodate the restraining portion 60 of the first component 14, the first component 14 may further include a base 64 extending distally from the stem 24 of the first component 14.

The restraining portion 60 may have any size and shape capable of providing restrained motion of the second component 18 with respect to the first component 14. For example, and as shown in FIG. 3, the restraining portion 60 may be in the form of a T shaped protrusion including a wide outer portion 66 and a narrow inner portion 68. Similarly, the cooperating portion 62 of the second component 18 may be in the form of a T shaped slot extending axially along the longitudinal axis 16 of the second component 18. As shown in FIG. 3, the T shaped protrusion 60 and the T shaped slot 62 may have uniform cross sections so that the second component 18 may freely move in the distal direction 69. The base 64 may include planar side walls 70 for cooperation with interior wall 72 of the second component 18.

The first component 14 and the second component 18 may be made of any suitable durable material and may be made of a sterilizable material such as a metal or a polymer. For example, the first component 14 and the second component 18 may be made of a stainless steel alloy, a cobalt chromium alloy, or a titanium alloy.

Figure 4:
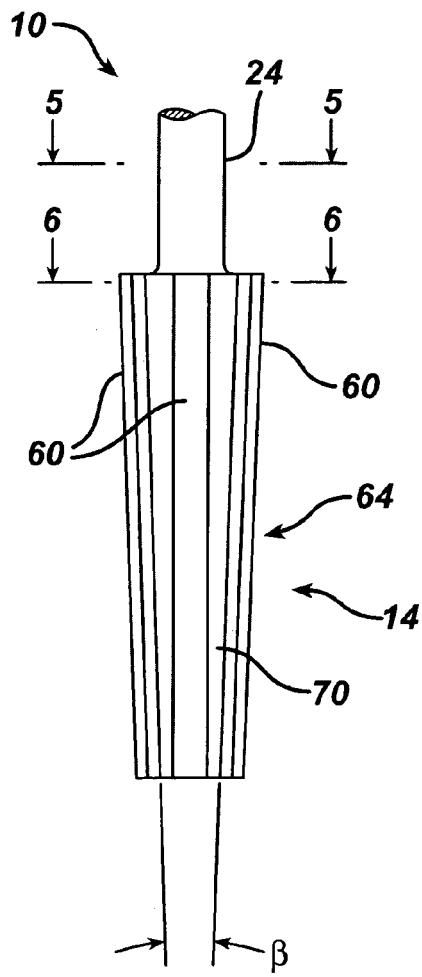
FIG. 4 is a partial plan view of the body of the instrument of FIG. 1.
Figure 5:
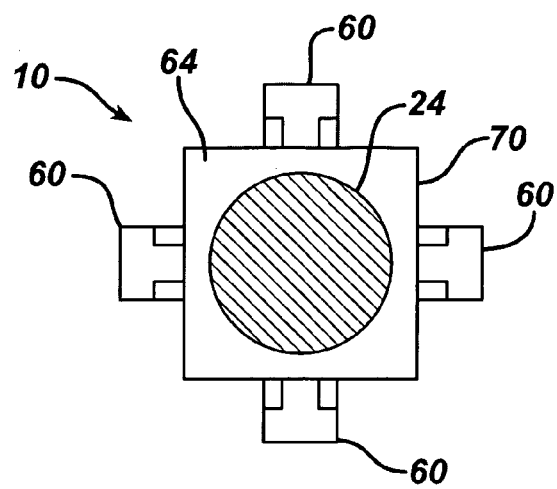
FIG. 5 is a partial top view of the body of FIG. 4 along the lines 5-5 in the direction of the arrows.
Figure 6:
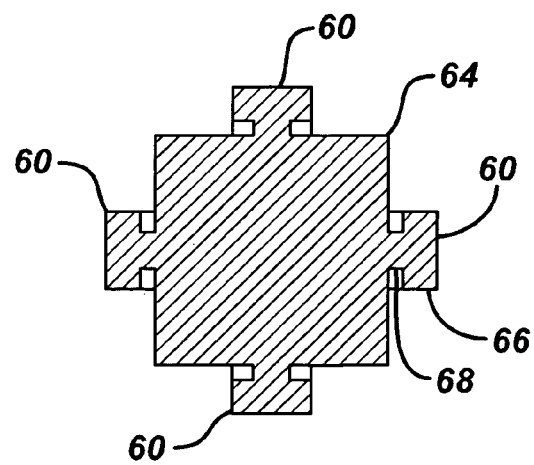
FIG. 6 is a cross sectional view of the body of the instrument of FIG. 4 along the lines of 6-6 in the direction of the arrows.

Referring now to FIGS. 4, 5, and 6, the protrusions 60 formed on the first component 14 are shown in greater detail. As shown in FIG. 4, the instrument 10 includes the first component 14 having a stem 24 and a base 64 extending from the stem 24. A series of axially extending protrusions 60 extend outwardly from the base 64. The base 64 is defined by a series as shown, of for example, four walls 70 defining the outer periphery of base 64. The walls 70 define an included angle β there between. The angle β provides outward movement of the second component 18 for packing of the bone material in the radial direction.

The angle β may be chosen to provide for the proper radial force in comparison of the axial force and for providing the proper radial movement for a respective axial movement of the instrument 10.

The radial force corresponding to an axial force for the instrument 10 may be defined by the following equation:

$$RF = AF \times \cotangent(\beta/2)$$

where:
RF=radial force
AF=axial force
β=the included angle

The included angle β may also be selected to provide for a corresponding relationship between radial displacement and axial displacement of the second component of the instrument 10 with respect to the first component of the instrument 10. The relationship of radial displacement to axial displacement may be defined by the following formula:

$$RD = AD \times \cotangent(\beta/2)$$

where:
RD=radial displacement
AD=axial displacement
β=the included angle

Referring now to FIGS. 5 and 6, the base 64 of the first component 14 of instrument 10 is shown greater detail. As shown in FIGS. 5 and 6, the base 64 may have a square cross section. It should be appreciated that the base 64 may have a rectangular cross section or have any shape. It should be appreciated that the instrument 10 should have one sliding surface or wall 70 corresponding to each of the sliding or second components. For example if the instrument includes three sliding components, the base would correspondingly be, for example triangular.

Figure 7:
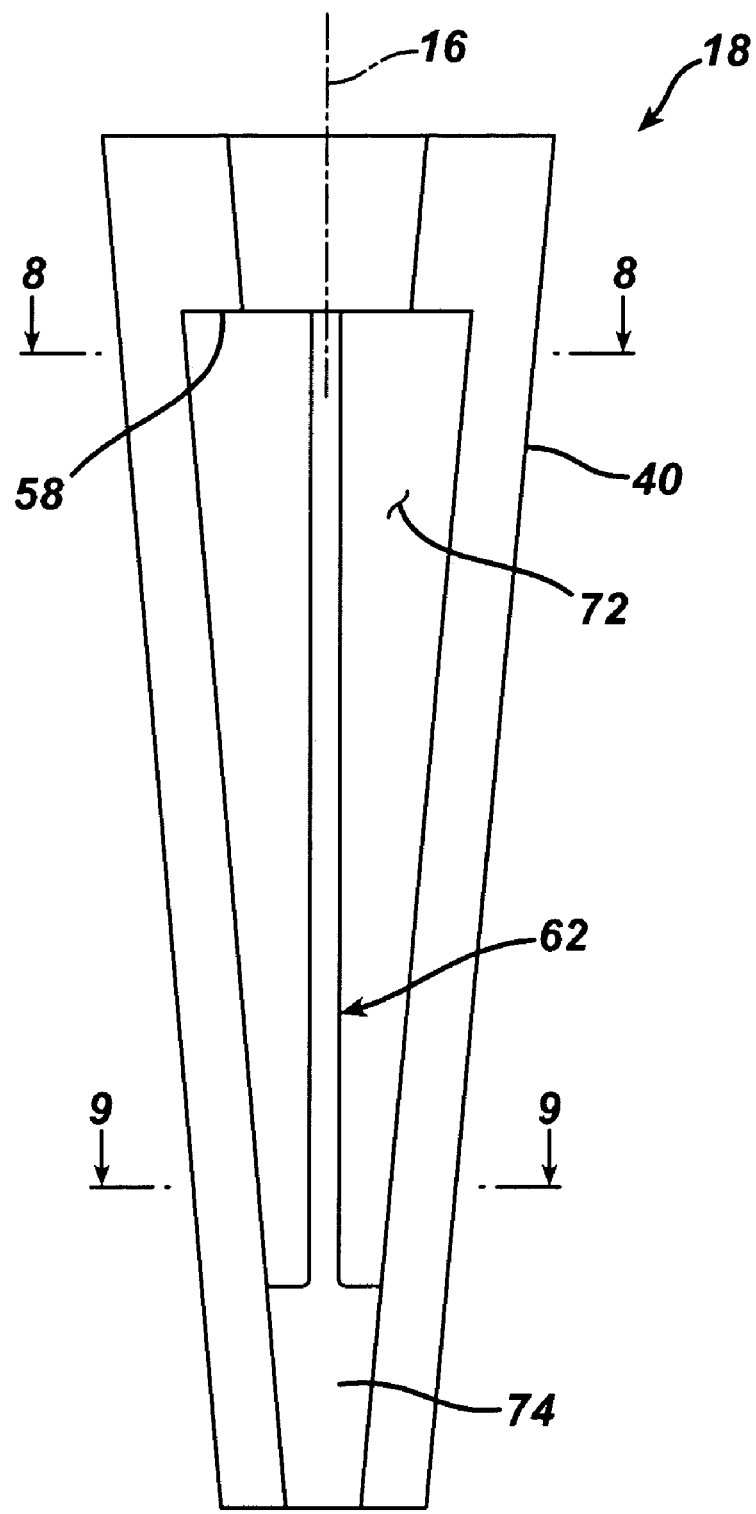
FIG. 7 is a plan view of a jaw of the instrument of FIG. 1.

Referring now to FIG. 7, the second component 18 is shown in greater detail. It should be appreciated that the second component 18 may, and as embodied in the instrument 10 of the present invention, include a plurality of identical moveable components, namely, third component 42, fourth component 44, and fifth component 46. Each of the components 18, 42, 44, and 46 are identical to each other. It should be appreciated that conversely the components may have different sizes and shapes.

The second component 18 is shown in greater detail in FIG. 7 and is illustrative of the size and shape of the third component 42 as well as the fourth and fifth components 44 and 46, respectively. The second component 18 includes a tapered arcuate periphery 40 and an opposed internal planar wall 72 for cooperation with one of the walls 70 of the base 64 of the first component 14 (see FIGS. 4-6). Second component 18 further includes the cooperating portion in the form of T-shaped slot 62 for cooperation with one of the T-shaped protrusions 60 of the first component 14. As shown in FIG. 7, the second component 18 may further include a distal lip 74 opposed to the proximal lip 58.

Figure 8:
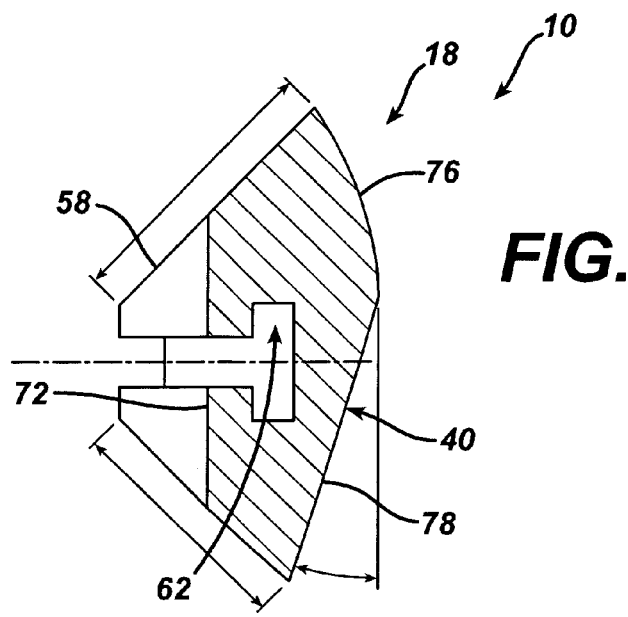
FIG. 8 is a cross sectional view of the jaw of FIG. 7 along the line 8-8 in the direction of the arrows.
Figure 9:
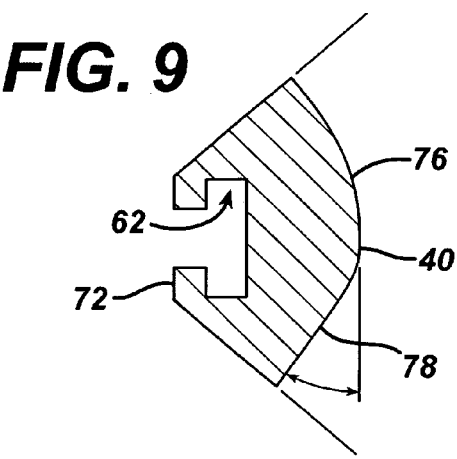
FIG. 9 is a cross sectional view of the jaw of FIG. 7 along the line 9-9 in the direction of the arrows.
Figure 9A:
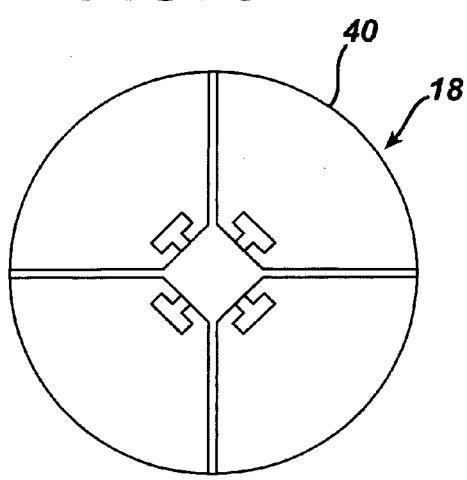
FIG. 9A is a bottom view of the instrument of FIG. 1.

Referring now to FIGS. 8, 9 and 9A, second component 18 is shown in greater detail. The second component 18 as shown in FIGS. 7, 8, 9 and 9A, may be tapered and may have a cross section that varies along the longitudinal axis 16 of the instrument 10. As shown in FIGS. 8 and 9, the outer periphery 40 of the first component 18 may be arcuate. For example, and as shown in FIGS. 8 and 9, the periphery 40 may include an arcuate first portion 76 and a linear portion 78. When four components such as second component 18 are combined to form the tamping portion 48 of the instrument 10, the arcuate portion 76 and the linear portions 78 cooperate to form, for example, a tamp with a rectangular cross section with rounded corners.

Figure 10:
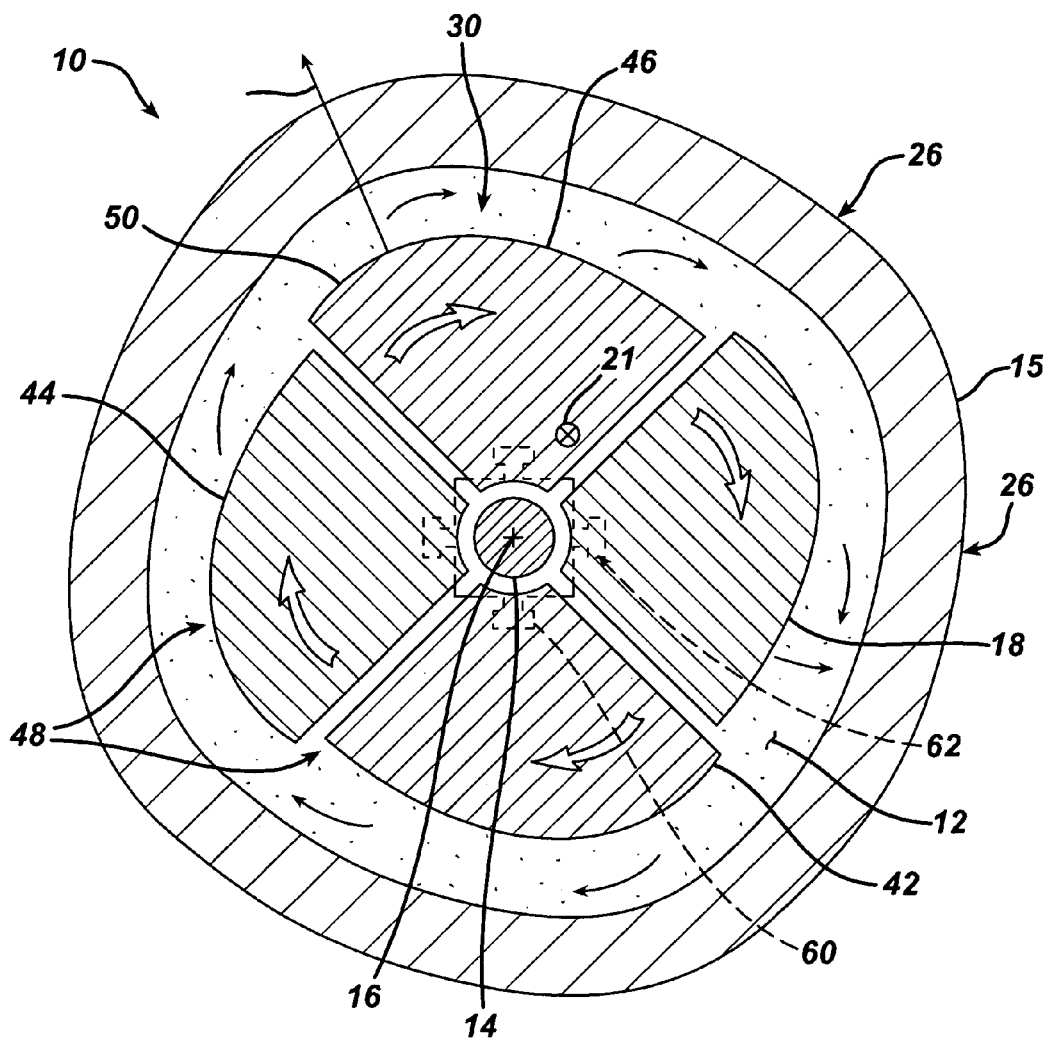
FIG. 10 is a cross sectional view of the instrument of FIG. 1 in position in the long bone along the line 10-10 in the direction of the arrows.

Referring now to FIG. 10, the instrument 10 is shown in position in long bone 26. Instrument 10 includes the first component 14 as well as component 18. As shown in FIG. 10, the instrument 10 is in position in the medullary canal 34 within the cortical bone 15 of the long bone 26. The bone material 12 is positioned between the cortical bone 15 and the periphery 50 of the tamping portion 48. As the tamping portion 48 advances along longitudinal axis 16 in the direction of arrow 21, the periphery 50 of the tamping portion 48 advances outwardly in the direction of arrow 23, thereby compressing or compacting the material 12.

If the periphery 50 of the tamping portion 48 is, as shown in FIG. 10, noncircular, the tamping portion 48 may be rotated in the direction of arrow 17 about longitudinal axis 16 to further compact the material 12.

Figure 1A:
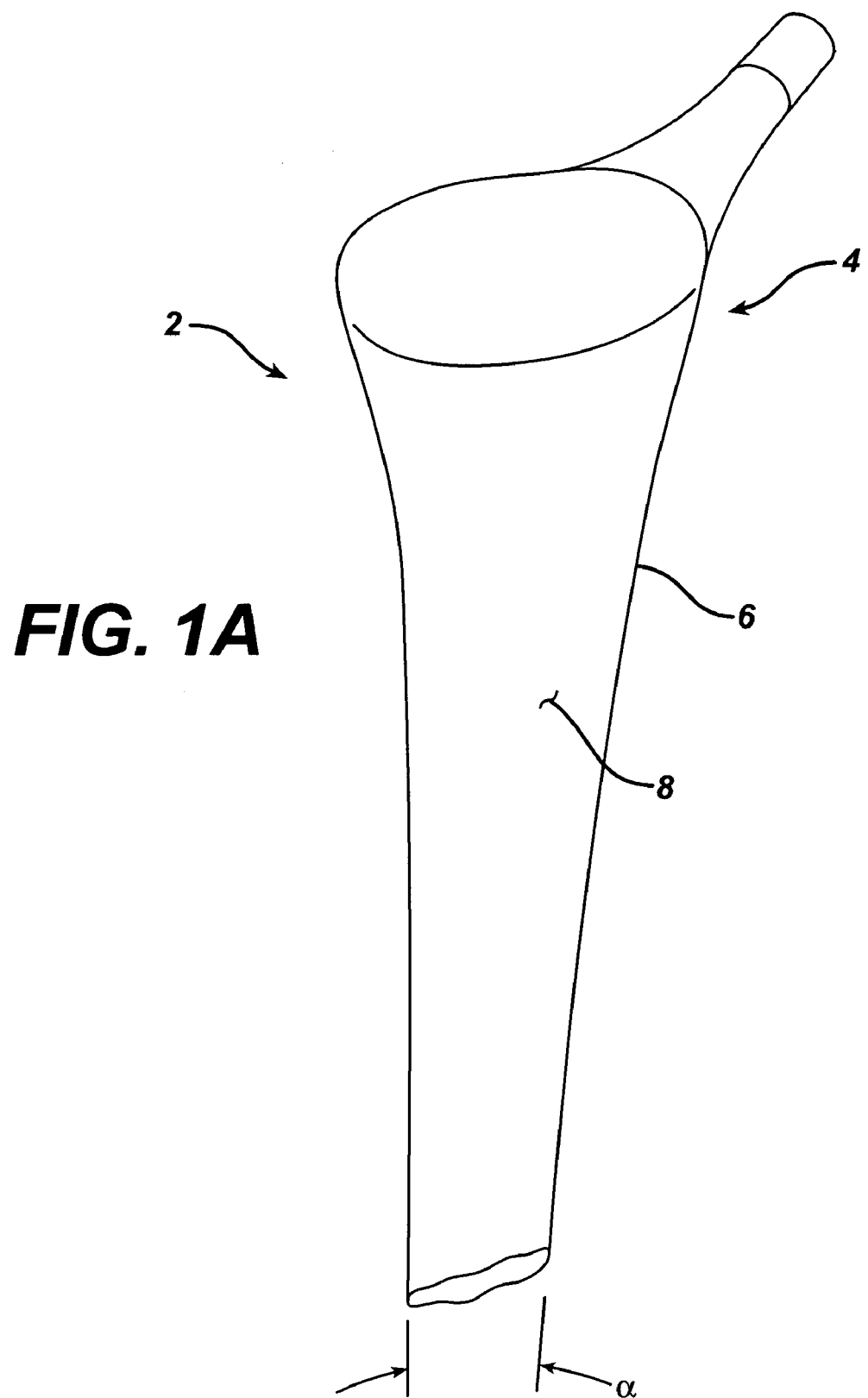
FIG. 1A is a plan view of a hip prosthesis for use with the instrument of the present invention.

It should be appreciated that the periphery 50 of the tamping portion 48 of the instrument 10 preferably replicates the shape of the corresponding part of the implant to be implanted. For example, as shown in FIG. 1A, the implant 2 is shown for use with the instrument 10. The implant 2 includes a distal portion 6 which has a distal portion implant periphery 8 which preferably has the same size and shape as the periphery 50 of the tamping portion 48 of the instrument 10. The distal portion 6 may define an included angle α. It should be appreciated that the present invention may be practiced with implants having an implant periphery of a variety of shapes including a generally rectangular square, round, triangular, or any suitable shape.

Figure 10A:
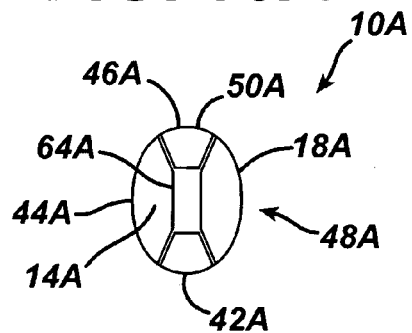
FIG. 10A is a cross sectional view of an alternate embodiment of the instrument of the present invention with an oval cross section.

For example and referring now to FIG. 10A, instrument 10A is shown. Instrument 10A is similar to instrument 10 except that base 64A of first component 14A has a generally rectangular cross section. Instrument 10A includes a second component 18A that is similar to the fourth component 44A and a third component 42A which is similar to the fifth component 46A. The components 18A, 42A, 44A and 46A define the periphery 50A of the tamping portion 48A. The periphery 50A of the instrument 10A is generally oval. The oval periphery 50A is of the instrument 10A is compatible for use with a stem (not shown) of a prosthesis which has an oval stem.

Figure 10B:
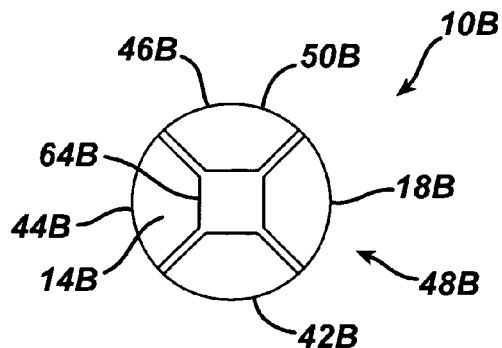
FIG. 10B is a cross sectional view of an alternate embodiment of the instrument of the present invention with an circular cross section.

Referring now to FIG. 10B, another embodiment of the present invention is shown as instrument 10B. Instrument 10B includes a first component 14B having a generally rectangular base 64B. Four additional components, namely, first component 18B, second component 42B, third component 44B and fourth component 46B combine to form the conformed tamping portion 48B defining a tamping portion periphery 50B. The periphery 50B of the tamping portion 48B of the instrument 10B is generally circular and compatible with a prosthesis having a circular cross section.

Figure 10C:
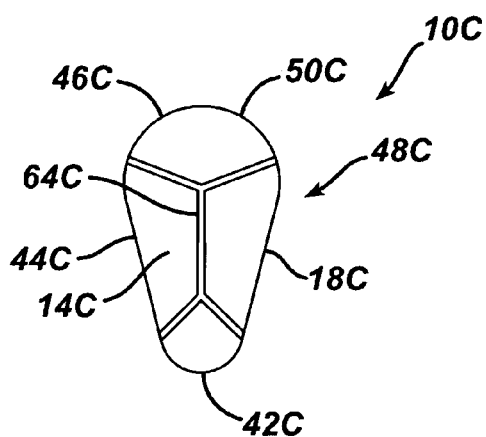
FIG. 10C is a cross sectional view of an alternate embodiment of the instrument of the present invention with an tapered oval cross section.

Referring now to FIG. 10C, another embodiment of the present invention is shown as instrument 10C. Instrument 10C is preferably for use with a prosthesis having a tapered oval cross section. The instrument 10C includes a first component 14C having a rectangular base 64C. Second component 18C, third component 42C, fourth component 44C, and fifth component 46C combine to form the tamping portion 48C defining the tamping portion periphery 50C. The tamping portion periphery 50C has a tapered oval shape corresponding to that of a implant having a tapered oval shape with which the instrument 10C would be utilized.

Figure 10D:
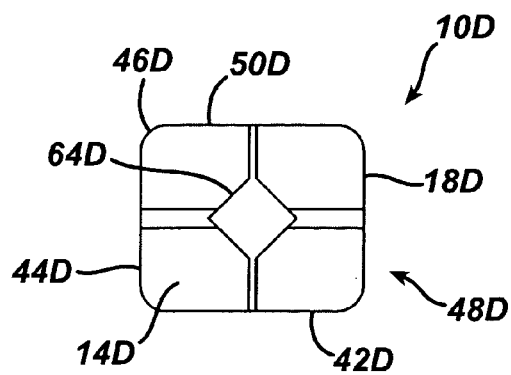
FIG. 10D is a cross sectional view of an alternate embodiment of the instrument of the present invention with an rectangular cross section.

Referring now to FIG. 10D, another embodiment of the present invention is shown in instrument 10D. Instrument 10D includes a first component 14D having a generally rectangular base 64D. Second component 18D, third component 42D, fourth component 44D, and fifth component 46D combine to form tamping portion 48D defining tamping portion periphery 50D. The tamping portion periphery 50D has a generally square cross section with the small radius at each corner of the square. The instrument 10D is preferable for use with a prosthesis having a stem with a generally square cross section with the corresponding radii at the corners.

Figure 10E:
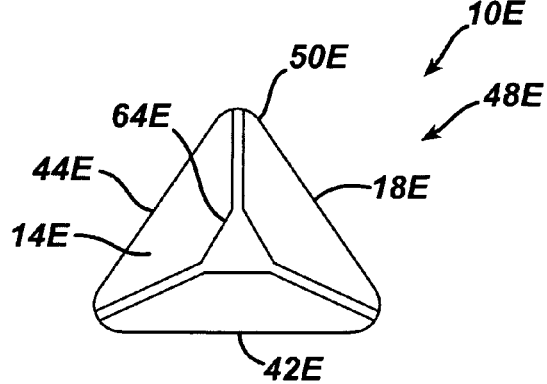
FIG. 10E is a cross sectional view of an alternate embodiment of the instrument of the present invention with an triangular cross section.

Referring now to FIG. 10E, another embodiment of the present invention is shown as instrument 10E. Instrument 10E includes a first component 14E including a base 64E. The base 64E has a generally triangular cross section. Second component 18E, third component 42E and fourth component 44E, combine to form the tamping portion 44E. The tamping 48E defines tamping portion outer periphery 50E. The tamping portion outer periphery 50E is generally triangular. The instrument 10E of FIG. 10E is compatible for use with a prosthesis having a triangular cross section.

Figure 11:
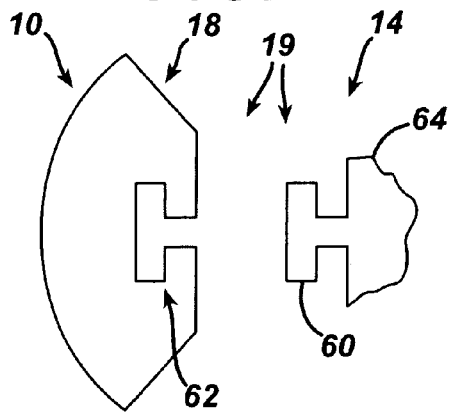
FIG. 11 is a partial cross sectional view of the instrument of FIG. 1 showing the sliding mechanism of the present invention in greater detail.

Referring now to FIG. 11, attachment 19 is shown for operatively associating the second component 18 with the first component 14. The attachment 19 may be any attachment able to provide the required relative motion between the first component 14 and the second component 18. For example, as shown in FIG. 11, the attachment 19 includes the T-shaped protrusion 18 extending from the base 64 of the first component 14. The attachment 19 further includes a T-shaped slot 62 for cooperating with the T-shaped protrusion 60. The T-shaped slot 62 is formed in, for example, second component 18. The T-shaped protrusion 60 and the T-shaped slot 62 cooperate to provide the attachment 19 providing relative motion of the second component 18 with respect to the first component 14.

Figure 11A:
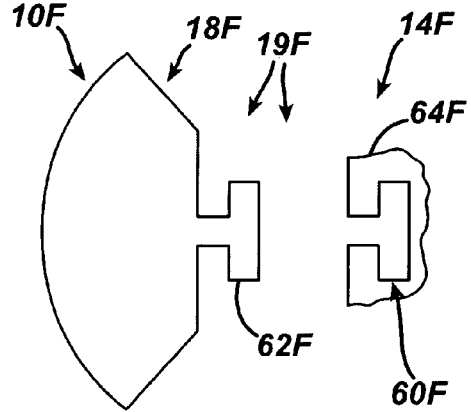
FIG. 11A is a partial cross sectional view of an alternate embodiment of an instrument according to the present invention with a sliding mechanism with a T-shaped tang in the jaw and a groove in the body.

It should be appreciated that the attachment 19 for providing relative motion of the second component 18 with respect to the first component 14 may be any suitable attachment. For example and referring now to FIG. 11A, the instrument of the present invention may be in the form of an instrument 10F. Instrument 10F may be similar to instrument 10 of FIGS. 1-10 and include, for example any attachment mechanism 19F which is the reverse of the attachment 19 of FIGS. 1-10. For example, the instrument 10F may include a first component 14F defining a base 64F. A slot 60F may be formed in the base 64. A T-shaped protrusion 62F may be formed in second component 18F. The protrusion 62F may be sized to cooperate with the slot 60F of the base 64.

Figure 11B:
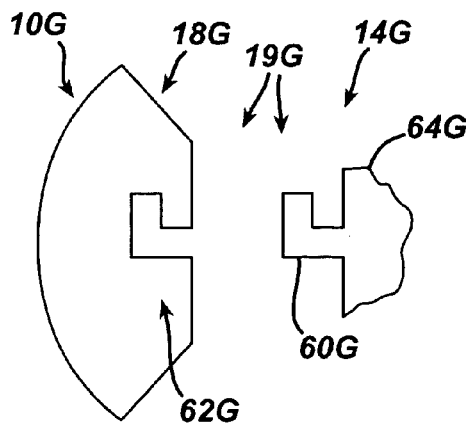
FIG. 11B is a partial cross sectional view of an alternate embodiment of an instrument according to the present invention with a sliding mechanism with an L-shaped groove in the jaw and a mating tang in the body.

Referring now to FIG. 11B, another embodiment of the present invention, is shown as instrument 10G. Instrument 10G is similar to instrument 10 of FIGS. 1-10 except that instrument 10G includes attachment mechanism 19G which is different that attachment mechanism 19 of FIGS. 1-10. For example, the instrument 10G includes an attachment mechanism 19G including an L-shaped protrusion 60G extending from base 64G of first component 14G. An L-shaped slot 62G is formed in second component 18G and cooperates with the protrusion 60G of the base 64 to provide the attachment mechanism 19G.

Figure 11C:
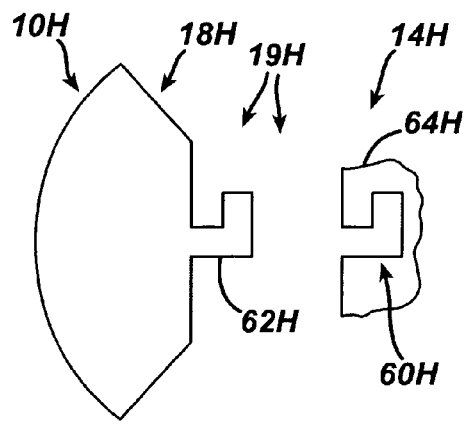
FIG. 11C is a partial cross sectional view of an alternate embodiment of an instrument according to the present invention with a sliding mechanism with an L-shaped tang in the jaw and a mating groove in the body.

Referring now to FIG. 11C, another embodiment of the present invention, is shown as instrument 10H. Instrument 10H is similar to instrument 10 of FIGS. 1-10 but includes an attachment mechanism 19H which is different. The attachment mechanism 19G includes an L-shaped protrusion 62 extending from second component 18 which cooperates with a slot 60H formed in base 64H of first component 14H. The protrusion 62H and the slot 60H combine to form the attachment mechanism 19H.

Figure 11D:
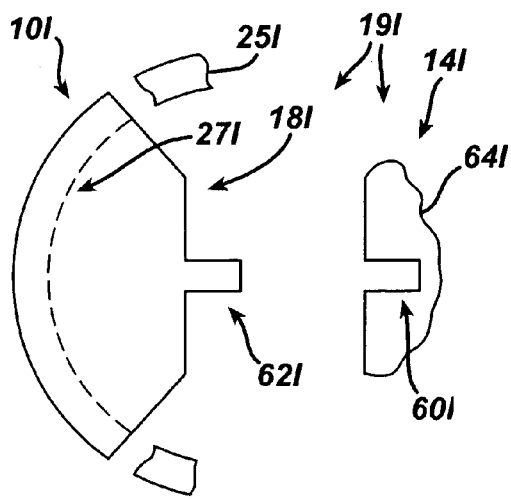
FIG. 11D is a partial cross sectional view of an alternate embodiment of an instrument according to the present invention with a sliding mechanism with a protrusion in the jaw, a mating slot in the body and a connecting band.

Referring now to FIG. 11D, it should be appreciated that the present invention may be practiced with an instrument in which the components do not interlock. For example and referring now to FIG. 11D, another embodiment of the present invention is shown as instrument 10I. Instrument 10I is similar to instrument 10 of FIGS. 1-10 but does not include an interlocking feature in the attachment of the components. For example, and as shown in FIG. 11D, the instrument 10I includes a first component 14I having a base 64I into which a slot 60I is formed. The slot 60I cooperates with a protrusion 62I formed second component 18I of the instrument 10I. The protrusion 62I of the second component 18I is in the form of a straight stem and does not include an interlocking feature. The instrument 10I may provide for interlocking of the components by, for example, including a groove 27I formed in the second component 18I into which a band 25I may be secured.

Figure 11E:
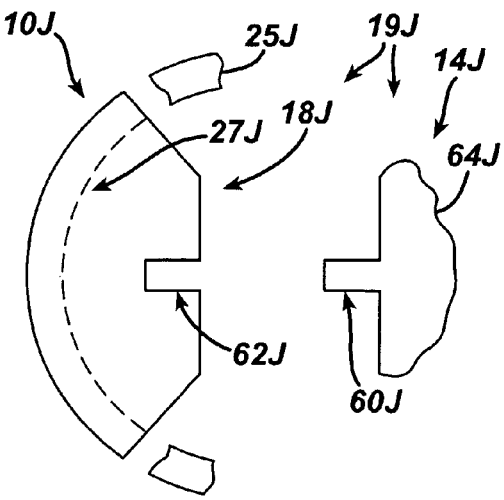
FIG. 11E is a partial cross sectional view of an alternate embodiment of an instrument according to the present invention with a sliding mechanism with a protrusion in the body, a mating slot in the jaw and a connecting band.

Referring now to FIG. 11E, another embodiment of the present invention is shown as instrument 10J. Instrument 10J is similar to instrument 10I of FIG. 11D except that instrument 10J includes an attachment mechanism 19J which is the reverse of attachment mechanism 19I of FIG. 10D. For example, the instrument 10J includes a first component 14J having a base 64J defining a protrusion 60J which mates with slot 62J formed in second component 18J. The instrument 10J may be similar to the instrument 10I of FIG. 11D and may include a band 25J positioned in groove 27J of the second component 18J.

Figure 11F:
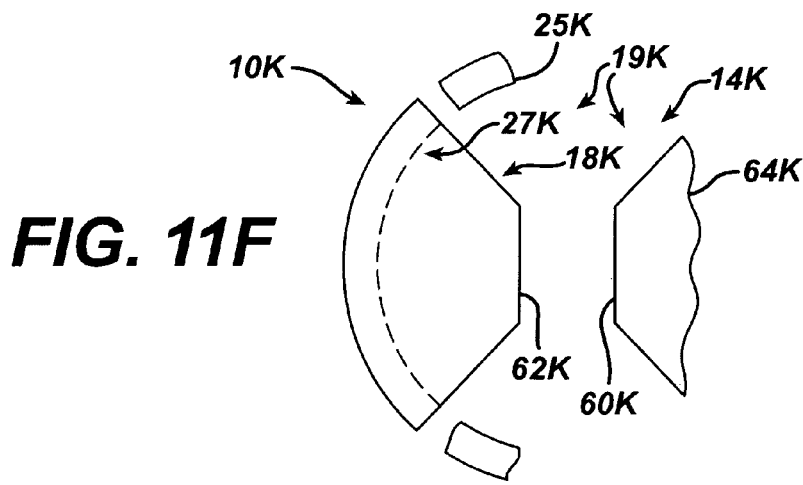
FIG. 11F is a partial cross sectional view of an alternate embodiment of an instrument according to the present invention with a sliding mechanism with a flat on the body, a mating flat on the jaw and a connecting band.

Referring now to FIG. 11F, another embodiment of the present invention is shown as instrument 10K. Instrument 10K is similar to instrument 10J of FIG. 11E except that a slot and protrusion is not used in the attachment mechanism. For example and as shown in FIG. 11F, the instrument 10K includes an attachment mechanism 19K having a first component 14K defining a base 64K having a base surface 60K which cooperates with a second component surface 62K formed on second component 18K. Surfaces 60K and 62K may be kept in contact by, for example, a band 25K positioned in groove 27K of the second component 18K. It should be appreciated that the band 25K as well as the bands 25I and 25J of instruments 10I and 10J of FIGS. 11D and 11E may be either slit or resilient to provide for the outward movement of the second component.

Figure 11G:
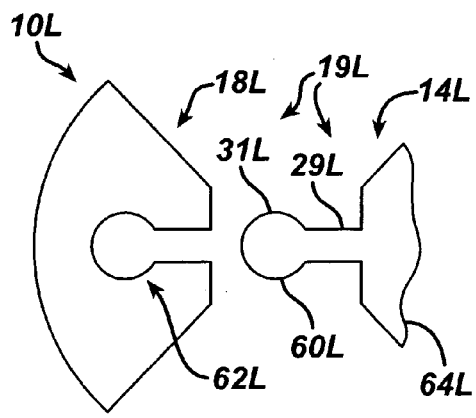
FIG. 11G is a partial cross sectional view of an alternate embodiment of an instrument according to the present invention with a sliding mechanism with a knob shaped protrusion in the body and a mating groove in the jaw.

Referring now to FIG. 11G, another embodiment of the present invention is shown as instrument 10L. Instrument 10L is similar to instrument 10 of FIGS. 1-10 except that instrument 10L includes a different attachment mechanism 19L. For example, the instrument 10L includes a first component 14L having a base 64L including a protrusion 60L having a stem portion 29L and a cylindrical portion 31L extending from the stem portion 29L. Instrument 10L further includes a second component 18L defining a slot 62L which cooperates with the protrusion 60L of the first component 14L.

Figure 11H:
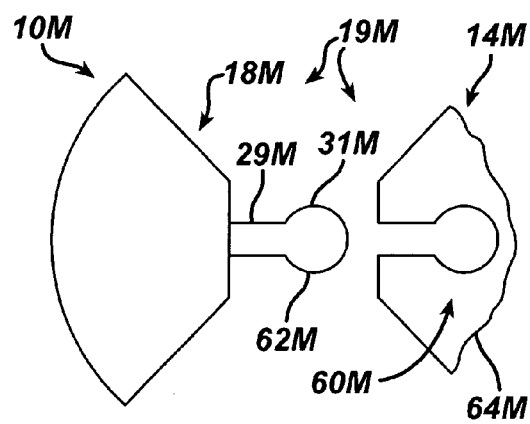
FIG. 11H is a partial cross sectional view of an alternate embodiment of an instrument according to the present invention with a sliding mechanism with a knob shaped protrusion in the jaw, and a mating groove in the body.

Referring now to FIG. 11H, another embodiment of the present invention is shown as instrument 10M. Instrument 10M is similar to the instrument 10L of FIG. 11G except that the attachment mechanism is reversed. For example, and as shown in FIG. 11H, the instrument 10M includes an attachment mechanism 19M including a protrusion 62M extending from second component 18M. The protrusion 62M includes a stem 29M to which a cylindrical portion 31M extends. The protrusion 62M cooperates with a slot 60M formed in base 64M of first component 14M.

Figure 11I:
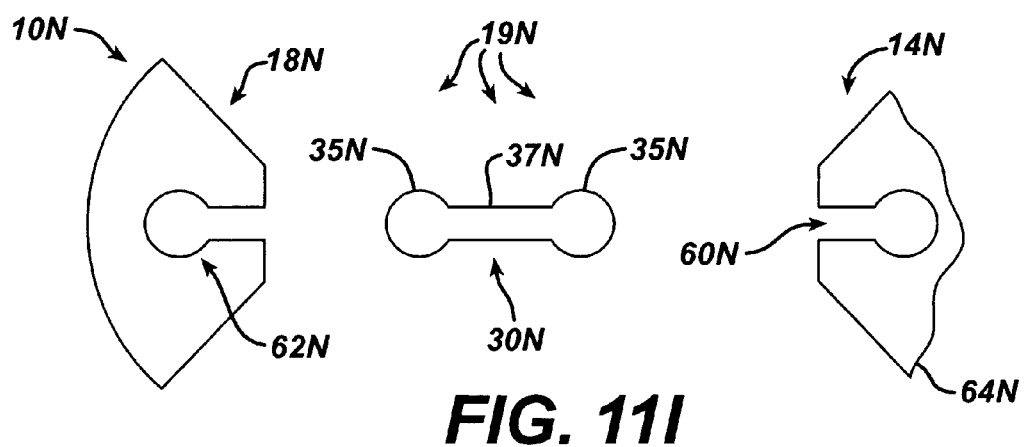
FIG. 11I is a partial cross sectional view of an alternate embodiment of an instrument according to the present invention with a sliding mechanism with a dog-bone shaped connection, a mating groove in the body and a mating groove in the jaw.

Referring now to FIG. 11I, another embodiment of the present invention is shown as instrument 10H. Instrument 10H is similar to the instruments 10L and 10M of FIGS. 11G and 11H, respectively. For example, the instrument 10N includes an attachment mechanism 19N having a three part construction. For example, the instrument 19N includes a first component 14N having a base 64N to which a first slot 60N is formed. The instrument 10N further includes a second component 18N to which a second slot 62N is formed. The slots 60N and 62N are connected with a connector 33N having opposed protrusions 35N and extending from the opposed ends of center portion 37N of the connector 33N. One protrusion 35N cooperates with first slot 60N while the other protrusion 35N cooperates with second slot 62N. The connector 33N may either be resilient or be permitted to articulate during the operation of the instrument 10N.

Figure 12:
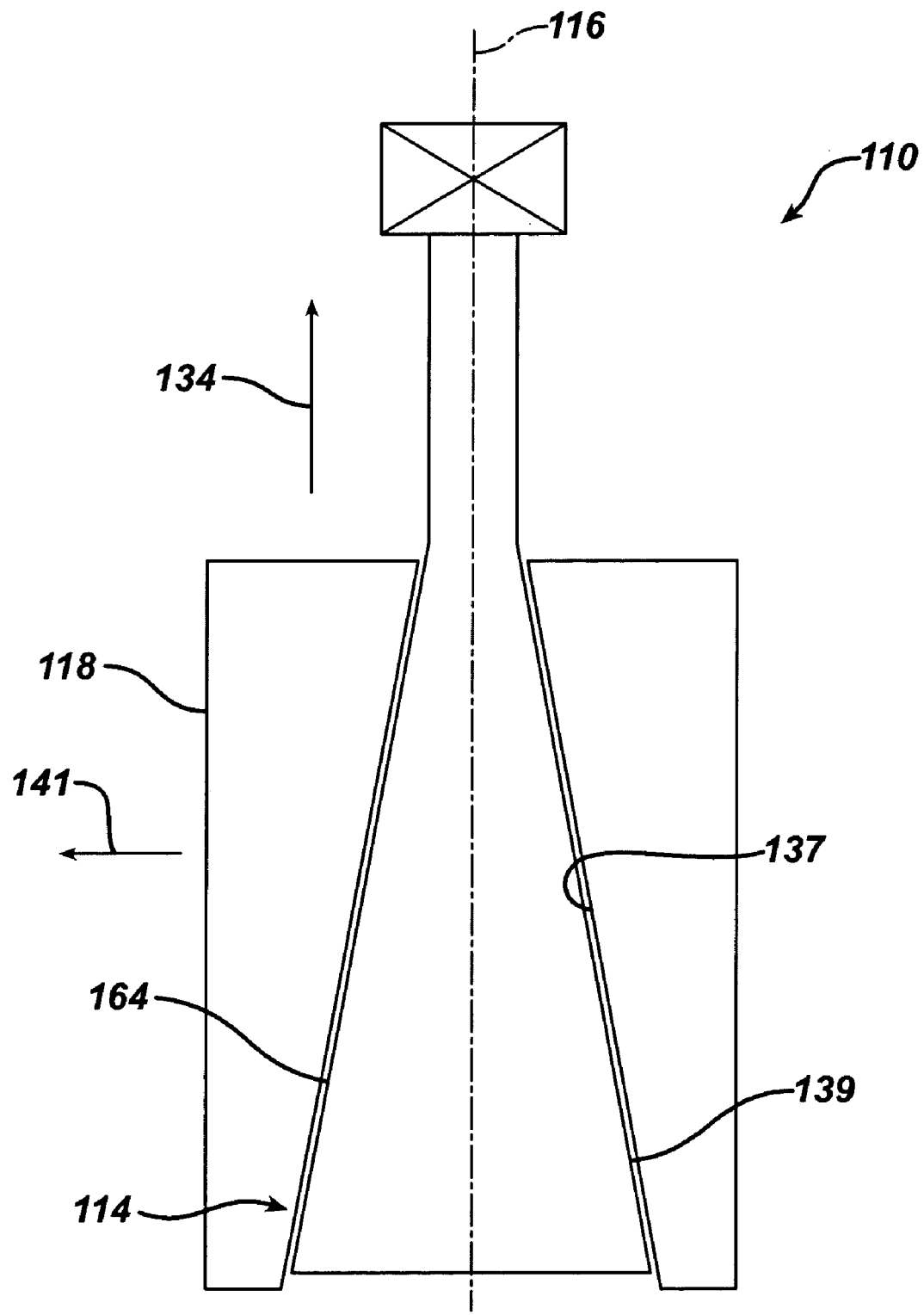
FIG. 12 is a partial cross sectional view of an alternate embodiment of an instrument according to the present invention with a reverse oriented tapered body.

While the instrument 10 of FIGS. 1-10 provides for compaction of the bone material when the instrument is advanced distally into the cavity, it should be appreciated that operation of the instrument of the present invention may operate in a reverse direction. For example, and referring now to FIG. 12, another embodiment of the present invention is shown as instrument 110. Instrument 110 is similar to instrument 10 of FIGS. 1-10 except that the instrument 110 includes a first component 114 having a base 164 defining external periphery 139 which has a reversed angle to that of the base 64 of the instrument 10 of FIGS. 1-10. The instrument 110 further includes a second component 118 having an internal periphery 137 which cooperates with the external periphery 139 of the base 164. As shown in FIG. 12 as the first component 114 is advanced in the direction of longitudinal axis 116 in the direction of arrow 134, the second component 118 advances transversely in the direction of arrow 141 to compress the bone material. The instrument of 110 of FIG. 12 operates in an opposite manner than that of the instrument 10 of FIGS. 1-10.

Figure 13:
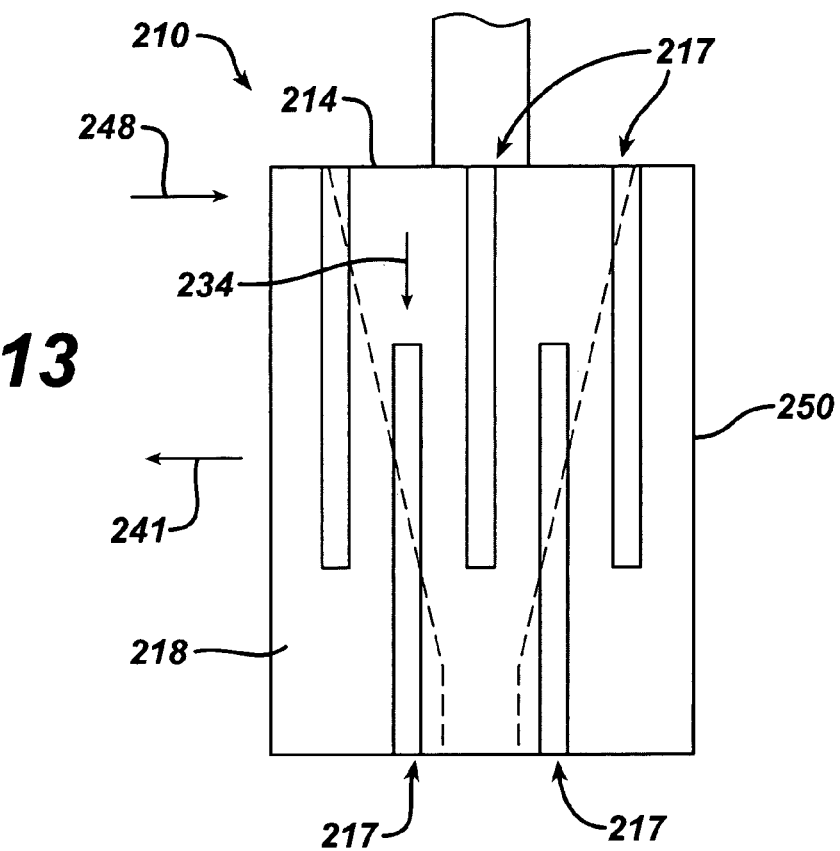
FIG. 13 is a partial plan view of an alternate embodiment of an instrument according to the present invention with a double split collet and a tapered body.

Referring now to FIG. 13, another embodiment of the present invention in the form of instrument 210 is shown. The instrument 210 is similar to the instrument 10 of FIGS. 1-10 except that it includes a tamping portion 248 in the form of a solitary component. As shown in FIG. 13, the instrument 210 includes a solitary tamping portion 248 in the form of a collet 218.

The second component 218 is in the form of a collet which cooperates with first component 218. Slots 217 are formed in periphery 250 of the second component 218. The slots 217 may extend from opposed ends of the collet 218. The slots 217 permit the expansion of the collet 218 in the direction of arrow 241 as the first component 214 advances in the direction of arrow 234 with respect to the collet 218.

Figure 14:
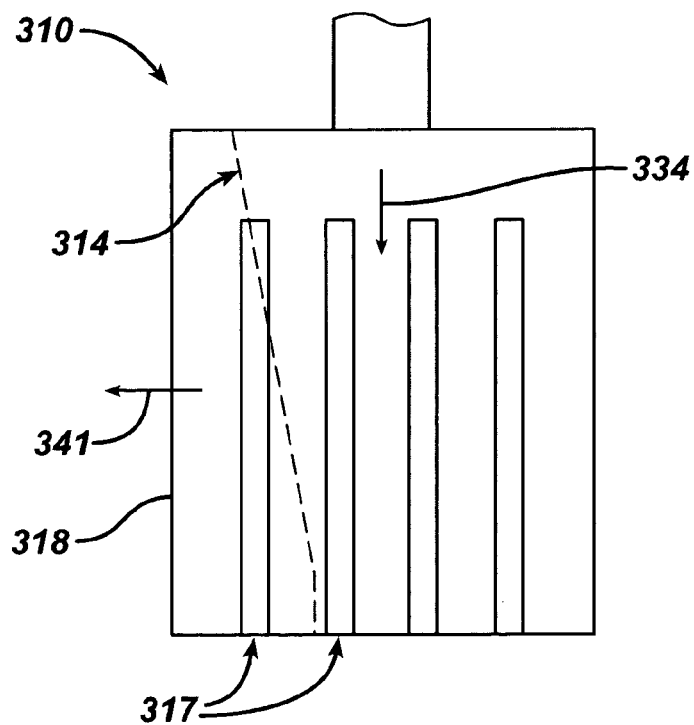
FIG. 14 is a partial plan view of an alternate embodiment of an instrument according to the present invention with a single split collet and a tapered body.

Referring now to FIG. 14 another embodiment of the present invention is shown as instrument 310. Instrument 310 is similar to instrument 210 of FIG. 13 except that the instrument 310 includes a collet 318 that includes slots 317 formed in only one end of the collet 318. The collet 318, similar to the collet 318, cooperates with a first component 314 to provide for motion of the collet 318 in the direction of arrow 341 as the first component 314 advances in the direction of arrow 334.

Figure 15:
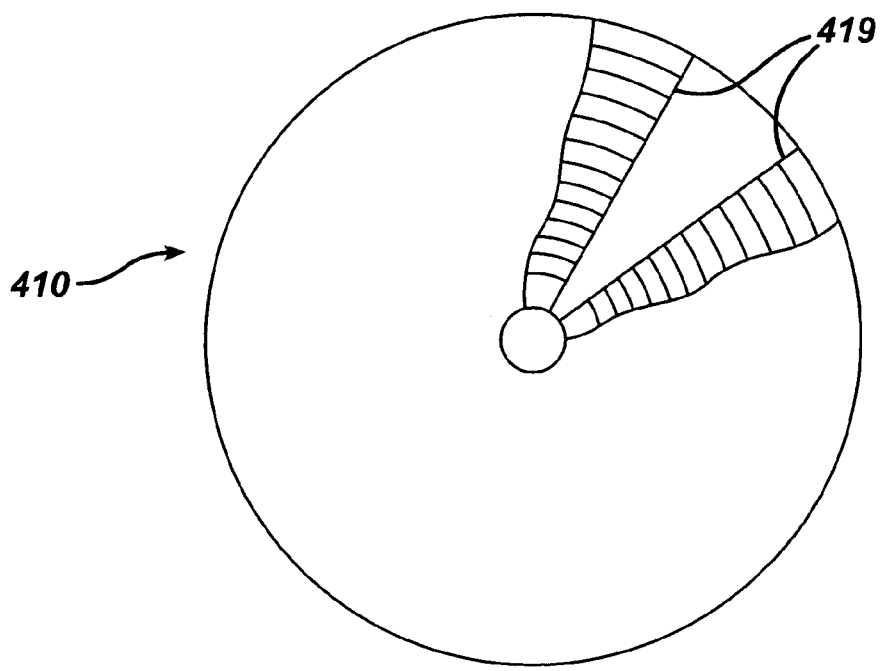
FIG. 15 is a top view partially in cross section of an alternate embodiment of an instrument according to the present invention with a series of split rings and a tapered body.
Figure 16:
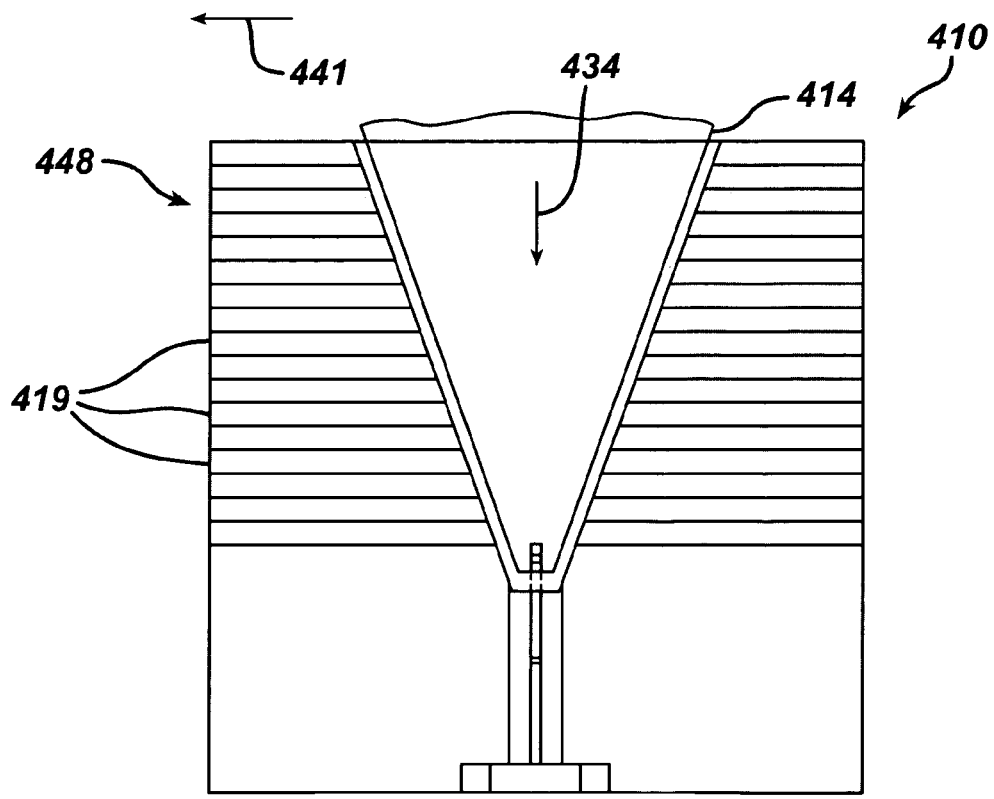
FIG. 16 is plan view partially in cross section of the instrument of FIG. 15.

Referring now to FIGS. 15 and 16 another embodiment of the present invention is shown as instrument 410. Instrument 410 is similar to instruments 210 and 310 of FIGS. 13 and 14, respectively in that instrument 410 relies on a resilient tamping portion. For example and as shown in FIGS. 15 and 16, the instrument 410 includes a tamping portion 448 including a plurality of spaced apart split rings 419 which combine to form the tamping portion 448. The rings 419 of the tamping portion 448 cooperate with first component 414. As first component 414 advances distally in the direction of arrow 434, the rings 419 expand outwardly in the direction of arrow 441, thereby compacting the bone material.

Figure 17:
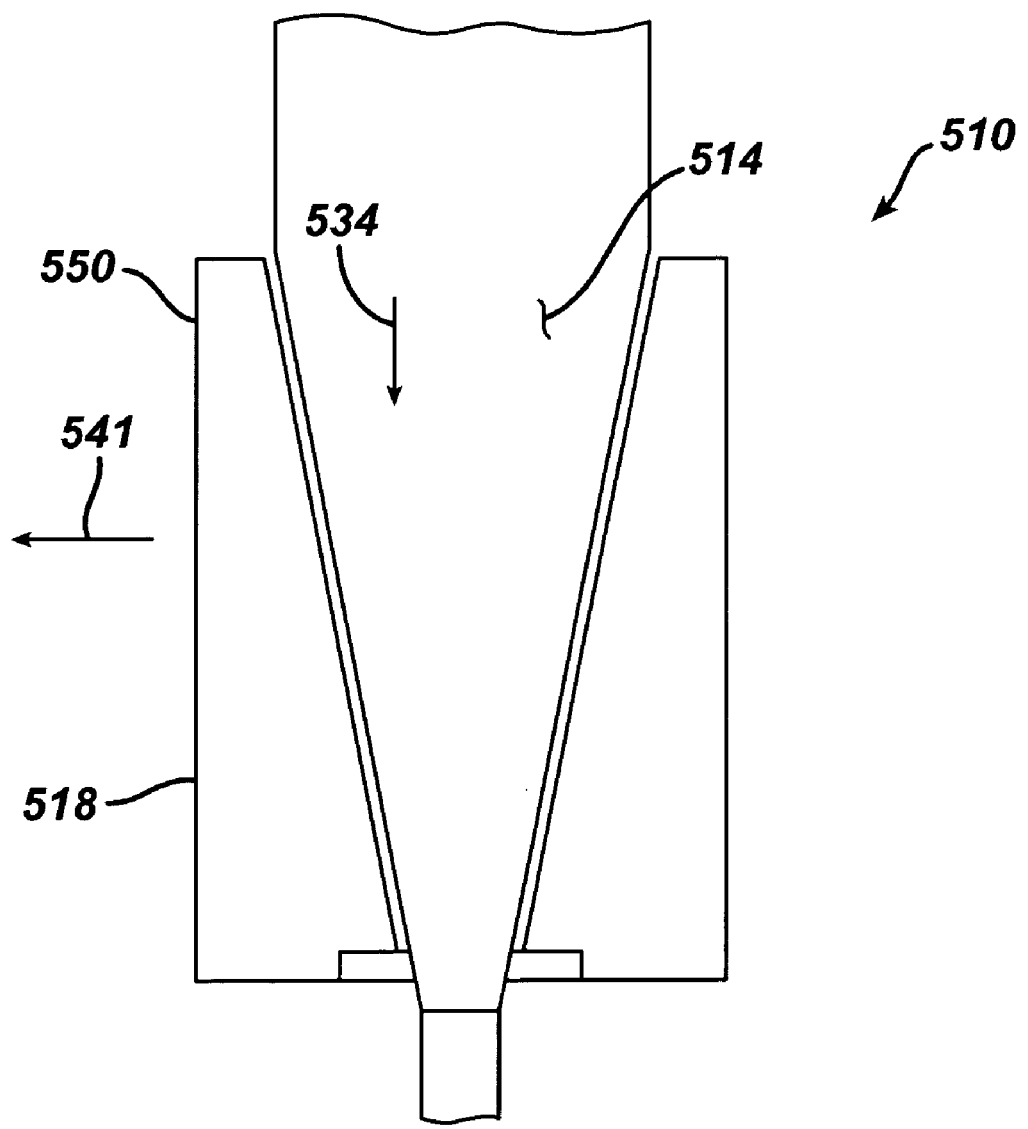
FIG. 17 is a plan view partially in cross section of an alternate embodiment of an instrument according to the present invention with a resilient collet and a tapered body.

Referring now to FIG. 17, another embodiment of the present invention is shown as instrument 510. Instrument 510 is similar to instrument 210 of FIG. 13 except that in the place of a collet with split components, a collet is provided made of a resilient material. For example and as shown in FIG. 17, the instrument 510 includes a second component 518 made of a resilient material, for example a polymer which is mately fitted to the first component 514. As the first component 514 advances downwardly in the direction of arrow 534, the resilient material in the second component 518 causes periphery 550 of the second component 518 to advance outwardly in the direction of arrow 541.

Figure 18:
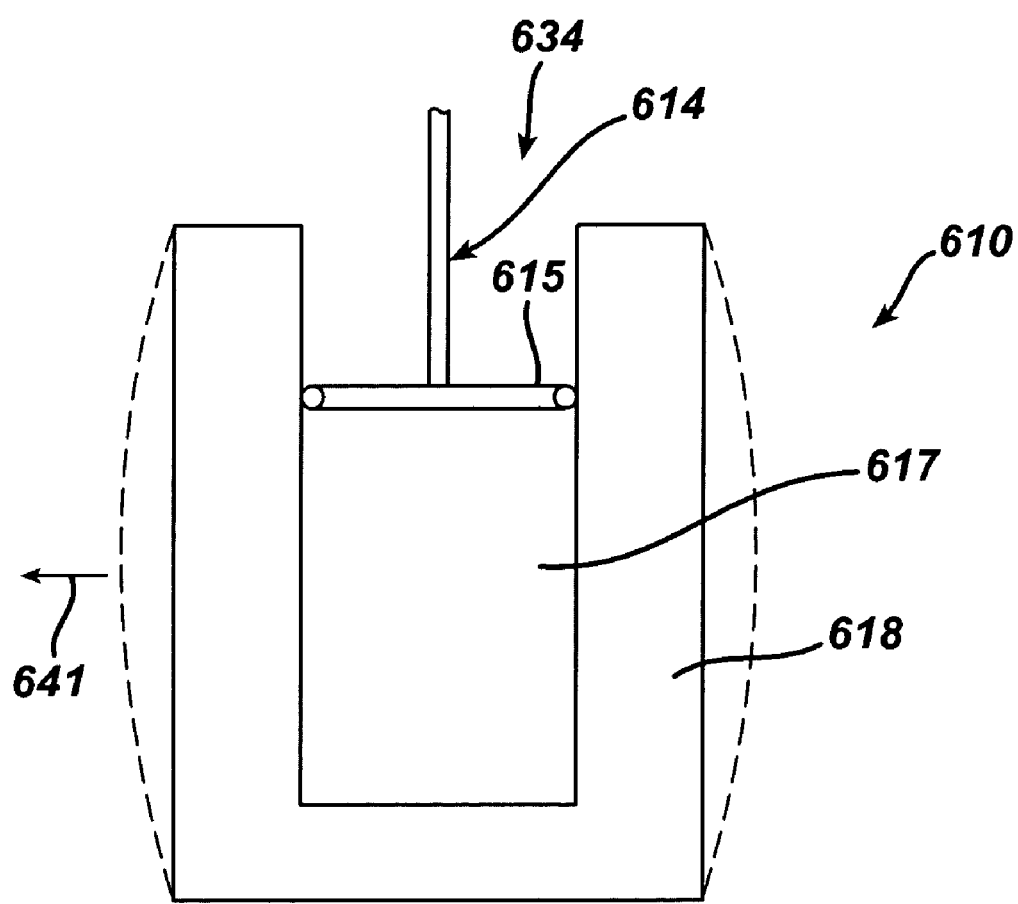
FIG. 18 is a plan view partially in cross section of an alternate embodiment of an instrument according to the present invention with a resilient collet and a hollow body filled with a fluid.

Referring now to FIG. 18, another embodiment of the present invention is shown as instrument 610. Instrument 610 is similar to instrument 510 of FIG. 17 in that the instrument 610 includes a second component 618 made of a resilient material. The resilient material of the second component 618 is expanded in a different method than that of the resilient material in the second component 518 of the instrument 510 of FIG. 17. For example and as shown in FIG. 18, the first component 614 cooperates with a piston 615 to advance a fluid 617 for expanding the second component 618. As first component 614 is advanced in the direction of arrow 634, the piston 615 is advanced in a similar direction compressing the fluid 618 outwardly in the direction of arrows 641 to expand the second component 618 thereby compacting the bone material.

Figure 19:
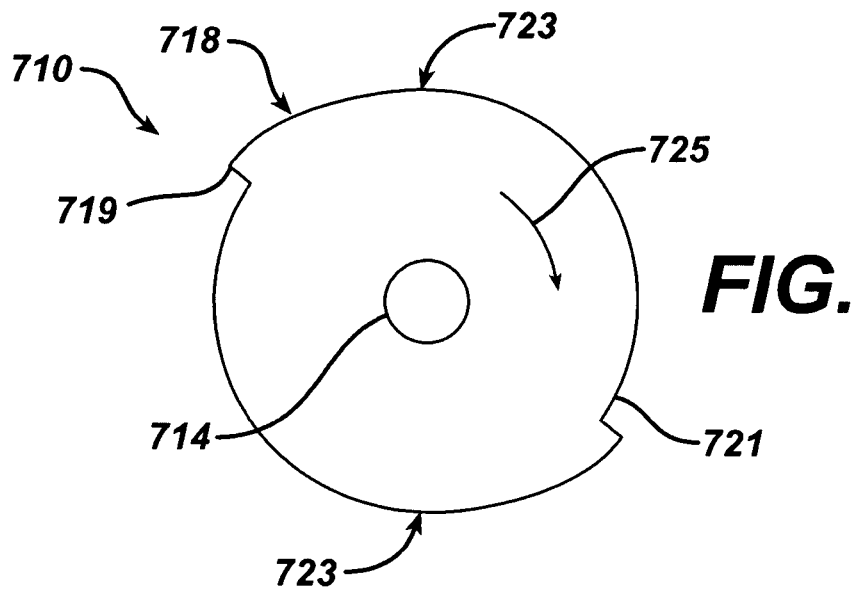
FIG. 19 is a perspective view of an alternate embodiment of instrument of the present invention with a generally cylindrical body with spiral portions on the periphery.
Figure 20:
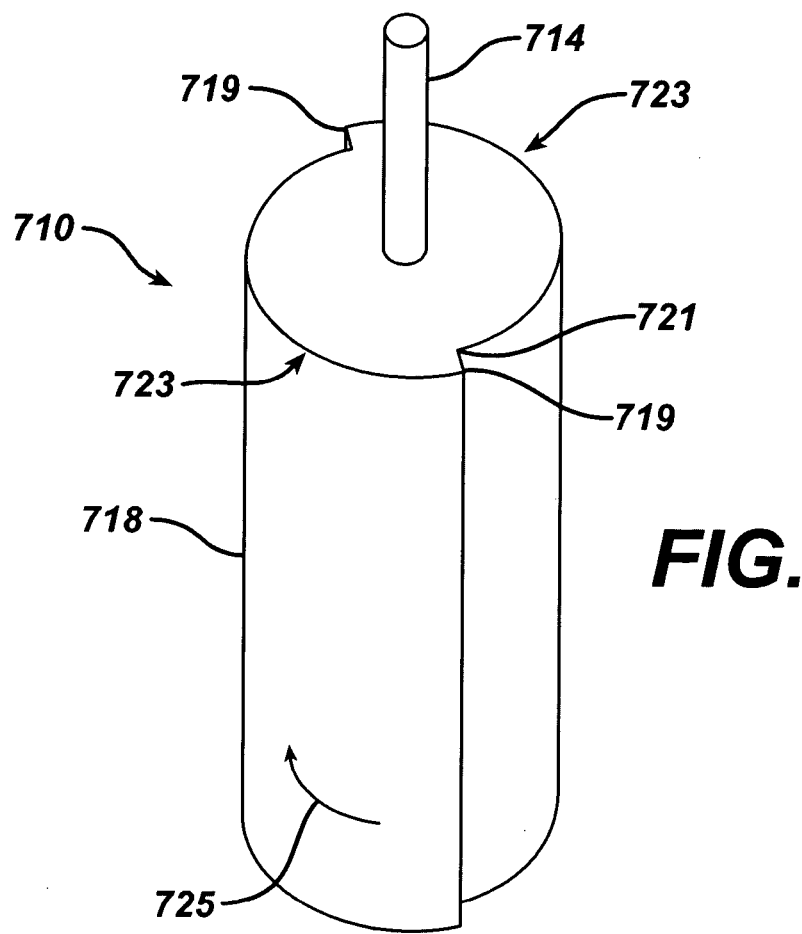
FIG. 20 is a top view of the instrument of FIG. 19.

Referring now to FIGS. 19 and 20, another embodiment of the present invention is shown as instrument 710. Instrument 710 includes a second component 718 extending distally from first component 714. The second component 718 is generally in the form of a cylinder but includes segments 723 extending outwardly from the second component 718. The segment 723 include a leading edge 721 and a trailing edge 719 which extends readily outward from the leading edge 721. As the instrument 710 is rotated in the direction of arrow 725, the second component 718 advances in the direction of arrow 725 causing bone material to advance from the leading edge 721 to a trailing edge 719 which provides for the compacting of the bone material.

Figure 21:
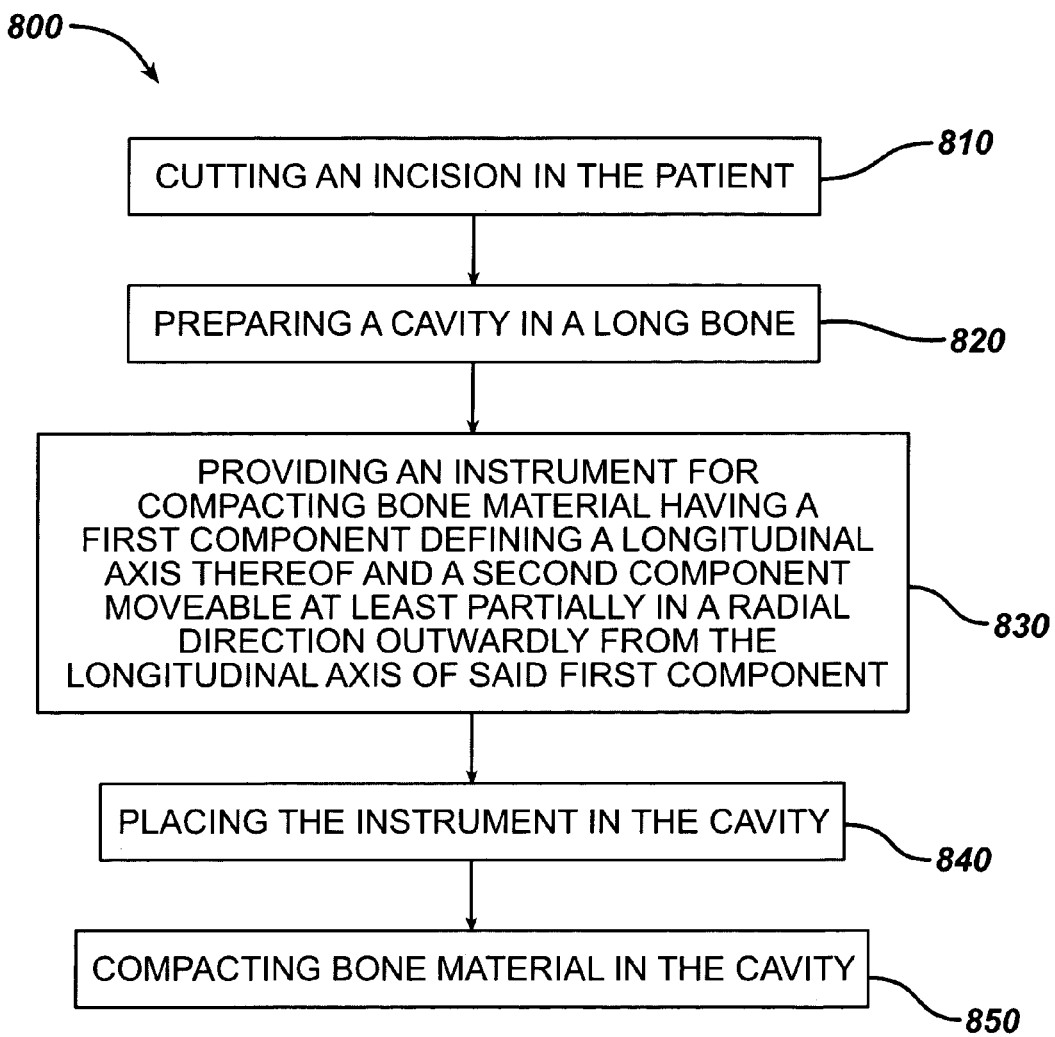
FIG. 21 is a flow chart of a method for performing arthroplasty in accordance with another embodiment of the present invention.

Referring now to FIG. 21, another embodiment of the present invention is shown as method 800. Method 800 includes the first step 810 of cutting an incision in the patient. The method 800 further includes a second step 820 of preparing a cavity in the long bone. The method 800 further includes a third step 830 of providing an instrument for compacting bone material having a first component defining a longitudinal axis thereof and a second component moveable at least partially in the radial direction outwardly from the longitudinal axis of the first component. The method 800 further includes a fourth step 840 of placing the instrument in a cavity and a fifth step 850 of compacting the bone material in the cavity.

Although the present invention and its advantages have been described in detail, it should be understood that various changes, substitutions, and alterations can be made therein without departing from the spirit and scope of the present invention as defined by the appended claims.

I claim:

1. An instrument for compacting bone material in preparation for inserting an implant, the implant having an outer periphery, said instrument comprising:
   a first component defining a longitudinal axis thereof, the first component including angled walls; and
   a second component and a third component, each of said second and third components moveably associated with said first component, said second component and said third component moveable at least partially in a radial direction outwardly from the longitudinal axis of said first component, wherein either said conical portion of said first component or both said second and third components define a groove and wherein the other of said conical portion of said first component said second and third components comprises a protrusion for cooperation with said groove, such that the protrusion extends into said groove, thereby coupling said first component to said second component and said third component, said second and third components slidingly engaged to said first component along said angled wall, such that as said angled wall is moved downwardly, said second and third components are pushed outwardly by said angled wall, said second component and said third component are completely separated from one another, such that said second component and said third component can move independently of one another;
   wherein said second and third components define an outer periphery, said outer periphery having a shape that generally replicates the outer periphery of the implant.

2. The instrument of claim 1, wherein said first component comprises:
   a body; and
   a stem extending from said body, said second component slidably mounted to said body.

3. The instrument of claim 1, wherein at least one of said first component and said second component is tapered along the longitudinal axis.

4. The instrument of claim 1:
   wherein said first component defines a restraining portion thereof; and
   wherein said second component defines a cooperating portion for cooperating with the restraining portion of said first component to provide restrained motion of said second component with respect to said first component.

5. The instrument of claim 1, wherein said second component defines a first surface for cooperation with the first component and a second surface opposed to the first surface for contact with the bone material.

6. The instrument of claim 5, wherein the second surface of said second component is adapted to urge the particles radially from the longitudinal axis as the first component is rotated about the longitudinal axis in a first direction.

7. The instrument of claim 1, wherein said first component and said second component are adapted to provide for motion of said second component away from the longitudinal axis of said first component as the first component is advanced axially in the direction of the longitudinal axis of said first component with respect to the second component.

8. An instrument for compacting bone material in a medullary canal of a long bone in preparation for inserting an implant, the implant having an outer periphery, said instrument comprising:

a first component defining a longitudinal axis thereof said first component having an outer periphery having angled walls, the outer periphery of said first component defining a restraining portion thereof; and a second component and a third component, each of said second and third components moveably associated with said first component, said second component and said third component defining a cooperating portion for cooperating with the restraining portion of said first component to provide restrained motion of said second component and said third component with respect to said first component, wherein one of said restraining portion of said first component and said second and third components defines a groove and wherein said other of said restraining portion of said first component and said second and third components comprises a protrusion for cooperation with said groove, such that the protrusion extends into said groove, thereby coupling said first component to said second component and said third component, said second and third components slidingly engaged to said first component along said angled wall, such that as said angled wall is moved downwardly, said second and third components are pushed outwardly by said angled wall, said second component and said third component are completely separated from one another, such that said second component and said third component can move independently of one another;

wherein said second component and third component define an outer periphery, said outer periphery having a shape that replicates the outer periphery of the implant.

9. The instrument of claim 8, wherein said first component comprises:

a body; and a stem extending from said body, said second component slidably mounted to said body.

10. The instrument of claim 8, wherein said second component defines a first surface for cooperation with the first component and a second surface opposed to the first surface for contact with the bone material.

11. The instrument of claim 10, wherein the second surface of said second component is adapted to urge the particles radially from the longitudinal axis as the first component is rotated about the longitudinal axis in a first direction.

12. The instrument of claim 8, wherein said first component and said second component are adapted to provide for motion of said second component away from the longitudinal axis of said first component as the first component is advanced axially in the direction of the longitudinal axis of said first component with respect to the second component.

* * * * *